US012151066B2

United States Patent
Duffy et al.

(10) Patent No.: US 12,151,066 B2
(45) Date of Patent: *Nov. 26, 2024

(54) AEROSOL CHAMBER AND INTERFACE TO OPTIMIZE INHALED DOSE WITH NEONATAL CPAP DEVICE

(71) Applicant: Stamford Devices Ltd., Dangan (IE)

(72) Inventors: Aidan Duffy, Galway (IE); Finbarr Maguire, Galway (IE); James B. Fink, San Mateo, CA (US)

(73) Assignee: Stamford Devices Ltd. Dangan, IE, Dangan (IE)

( * ) Notice: Subject to any disclaimer, the term of this patent is extended or adjusted under 35 U.S.C. 154(b) by 839 days.

This patent is subject to a terminal disclaimer.

(21) Appl. No.: 16/883,678

(22) Filed: May 26, 2020

(65) Prior Publication Data

US 2020/0368483 A1    Nov. 26, 2020

Related U.S. Application Data

(60) Provisional application No. 62/852,867, filed on May 24, 2019, provisional application No. 62/852,862, filed on May 24, 2019.

(51) Int. Cl.
*A61M 16/14* (2006.01)
*A61M 11/00* (2006.01)
(Continued)

(52) U.S. Cl.
CPC .......... *A61M 16/14* (2013.01); *A61M 11/001* (2014.02); *A61M 15/009* (2013.01);
(Continued)

(58) Field of Classification Search
CPC .............. A61M 16/14; A61M 16/0883; A61M 16/0816; A61M 16/0875; A61M 16/0666;
(Continued)

(56) References Cited

U.S. PATENT DOCUMENTS 6,530,370 B1 *  3/2003  Heinonen ......... A61M 15/0085
                                                      239/338
7,971,588 B2    7/2011  Fink et al.
                 (Continued)

FOREIGN PATENT DOCUMENTS

EP     3 277 355 A1     2/2018
JP    2008511398 A      4/2008
            (Continued)

OTHER PUBLICATIONS

International Preliminary Report on Patentability for PCT/US2020/034575 issued Nov. 16, 2021, all pages.

(Continued)

*Primary Examiner* — Joseph D. Boecker
*Assistant Examiner* — Brian T Khong
(74) *Attorney, Agent, or Firm* — Kilpatrick Townsend & Stockton LLP

(57) ABSTRACT

An aerosolization system includes a respiration system having an inspiratory limb and an expiratory limb. The system includes an aerosol chamber coupled with the inspiratory limb via a fluid channel. The fluid channel is disposed such that the aerosol chamber is isolated from continuous flow passing through the respiratory system. The system includes a patient interface positioned at a first location of the aerosol chamber and an aerosolization device positioned at a second location of the aerosol chamber positioned opposite the first location. The aerosolization device includes a reservoir that receives a volume of liquid medicament for aerosolization by the aerosolization device. The aerosol chamber mixes aerosolized medicament from the aerosolization device with respiratory flow received from the respiration system via the fluid channel.

25 Claims, 24 Drawing Sheets

(51) Int. Cl.
  *A61M 15/00* (2006.01)
  *A61M 16/04* (2006.01)
  *A61M 16/06* (2006.01)
  *A61M 16/08* (2006.01)
  *A61M 39/10* (2006.01)

(52) U.S. Cl.
  CPC .... *A61M 16/0465* (2013.01); *A61M 16/0488* (2013.01); *A61M 16/0666* (2013.01); *A61M 16/0816* (2013.01); *A61M 16/0883* (2014.02); *A61M 11/005* (2013.01); *A61M 2039/1077* (2013.01); *A61M 2202/0488* (2013.01); *A61M 2205/0294* (2013.01); *A61M 2205/3379* (2013.01); *A61M 2205/581* (2013.01); *A61M 2205/583* (2013.01); *A61M 2205/8206* (2013.01); *A61M 2230/40* (2013.01); *A61M 2240/00* (2013.01)

(58) Field of Classification Search
  CPC ............ A61M 16/0833; A61M 11/001; A61M 11/002; A61M 11/005; A61M 11/02; A61M 15/0085; A61M 2039/1077
  See application file for complete search history.

(56) References Cited

U.S. PATENT DOCUMENTS

| | | | |
|---|---|---|---|
| 8,196,573 | B2 | 6/2012 | Fink et al. |
| 8,701,658 | B2 | 4/2014 | Mazela et al. |
| 8,985,100 | B2 | 3/2015 | Minocchieri et al. |
| 9,308,333 | B2 | 4/2016 | Minocchieri et al. |
| 2002/0020412 | A1* | 2/2002 | Gilbert .............. A61M 16/0833 128/203.12 |
| 2005/0217666 | A1* | 10/2005 | Fink ........................ A61P 31/10 128/200.14 |
| 2011/0108025 | A1* | 5/2011 | Fink .................. A61M 15/0085 128/200.23 |
| 2012/0125334 | A1 | 5/2012 | Korneff et al. |
| 2013/0146053 | A1* | 6/2013 | Mazela ............. A61M 16/0858 137/15.01 |
| 2013/0174840 | A1 | 7/2013 | Gallem et al. |
| 2015/0165146 | A1 | 6/2015 | Bowman et al. |
| 2016/0130715 | A1* | 5/2016 | Xu ............................ C25D 3/48 205/122 |
| 2018/0169691 | A1 | 6/2018 | Macloughlin et al. |
| 2018/0272079 | A1 | 9/2018 | Porter et al. |

FOREIGN PATENT DOCUMENTS

| | | |
|---|---|---|
| JP | 2011519642 A | 7/2011 |
| WO | 2006-026237 A1 | 3/2006 |
| WO | 2006-102345 A2 | 9/2006 |
| WO | 2016/198667 | 12/2016 |
| WO | 2018-034574 A1 | 2/2018 |
| WO | 2018-172563 A1 | 9/2018 |
| WO | 2019-115771 A1 | 6/2019 |

OTHER PUBLICATIONS

Examination Report for EP 18 714 745.9 dated May 21, 2021, all pages.
International Search Report and Written Opinion mailed Sep. 8, 2020 in corresponding application No. PCT/US2020/034575; all pages.
Office Action for Japanese Appln No. 2021-569473 issued Dec. 19, 2023, all pages.
First Office Action for Chinese Appln No. 202080038282.8, all pages.

* cited by examiner

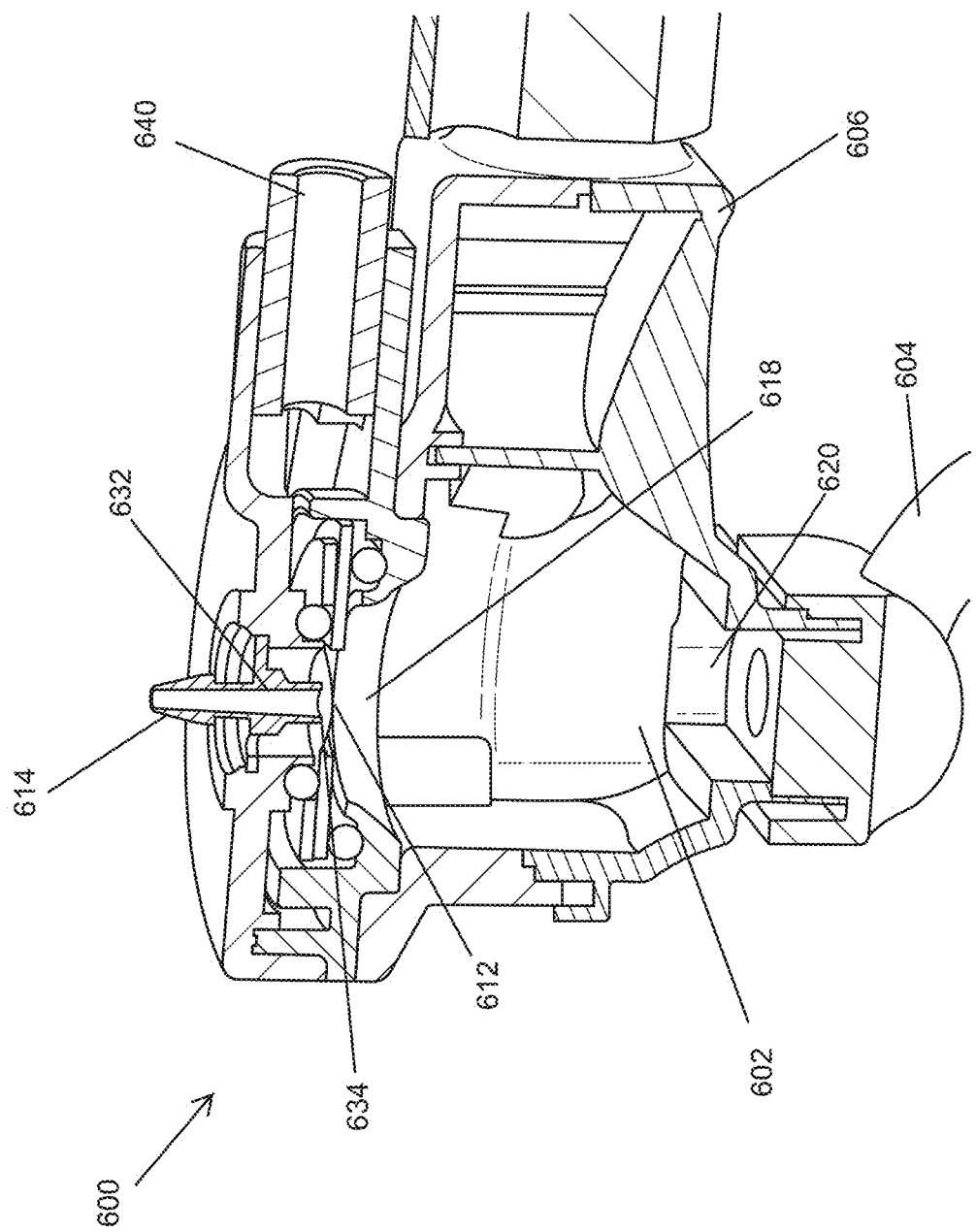

AEROSOL CHAMBER AND INTERFACE TO OPTIMIZE INHALED DOSE WITH NEONATAL CPAP DEVICE

CROSS REFERENCE TO RELATED APPLICATIONS

This application claims priority to U.S. Provisional Application No. 62/852,867, filed on May 24, 2019, entitled Design Of Aerosol Chamber And Interface To Optimize Inhaled Dose With Neonatal CPAP Device and U.S. Provisional Application No. 62/852,862, filed on May 24, 2019, entitled Design Of Aerosol System And Interface To Deliver Clinically And Economically Feasible Inhaled Dose With Neonatal CPAP Device, the entire contents of which are hereby incorporated by reference.

This application is related to U.S. application Ser. No. 15/933,205, filed on March 22, 2018, entitled Aerosol Delivery Device, U.S. application Ser. No. 15/933,217, filed on Mar. 22, 2018, entitled Retrofit Aerosol Delivery System and Method, U.S. application Ser. No. 15/933,219, filed on Mar. 22, 2018, entitled Aerosol Delivery System and Method, U.S. Application No. 62/475,618, filed Mar. 23, 2017, entitled Retrofit Aerosol Delivery System and Method, U.S. Application No. 62/475,635, filed Mar. 23, 2017, entitled Aerosol Delivery Device, and U.S. Application No. 62/475,603, filed Mar. 23, 2017, entitled Aerosol Delivery System and Method, the entire contents of which are incorporated by reference herein.

BACKGROUND

Conventional interfaces for nasal CPAP consist of gas inlet from inspiratory limb and outlet to expiratory limb, with an interface to patient via nasal prongs or mask. For example, conventional systems allow aerosol to be introduced though a secondary port prior to the inspiratory limb with the aerosol flow being directed through a separate conduit to the patient interface. Such solutions require continuous aerosol generation and gas flow. By placing an aerosol generator between the gas flow and patient interface, the delivery of medicament can vary significantly based on the gas flow rate of the respiration system. For example, with lower system gas flow (~0.5 L/min) the inhaled dose may be upwards 30-45%, but with high system gas flows (>6 L/min) the inhaled dose may be reduced to less than 6%. More consistent drug delivery systems are desired.

SUMMARY

Embodiments of the invention provide aerosolization systems and methods in which aerosolized medicament and respiratory gases are mixed within an aerosolization chamber prior to being introduced into a patient's airway. The aerosolization chamber may be isolated from a primary flow path of the respiration system. In other words, the respiratory gases present within the aerosolization chamber are intermittent, being drawn in only by the patient's inhalation rather than continuously being pushed into the chamber by the respiration system. Such designs help maintain consistent drug delivery results, as flow rate variance is reduced.

In one aspect, an aerosolization system is provided. The aerosolization system includes a respiration system having an inspiratory limb and an expiratory limb. The system may also include an inlet coupled with the inspiratory limb of the respiration system. The system may further include an aerosol chamber coupled with the inlet via a fluid channel. The fluid channel may be disposed such that the aerosol chamber is isolated from continuous flow passing through the respiration system. The system may also include a patient interface positioned at a first end of the aerosol chamber and an aerosolization device positioned at a second end of the aerosol chamber opposite the first end. The aerosolization device may include a reservoir that is configured to communicate medicament to the mesh of the aerosol generator and/or to receive a volume of liquid medicament for aerosolization by the aerosolization device. The aerosol chamber may be configured to mix aerosolized medicament from the aerosolization device with respiratory flow received from the respiration system via the fluid channel.

In another aspect, an aerosolization system includes an aerosol chamber and an aerosolization device positioned at a first end of the aerosol chamber. The aerosolization device may include a reservoir that is configured to receive a volume of liquid medicament for aerosolization by the aerosolization device. The system may also include an inlet, an outlet, and a fluid channel coupling the aerosol channel with one of the inlet or the outlet. The fluid channel may be disposed such that the aerosol chamber is isolated from continuous flow passing from the inlet to the outlet. The aerosol chamber may be configured to mix respiratory flow received from the respiration system via the fluid channel with aerosolized medicament from the aerosolization device.

In another aspect, a method of delivering aerosolized medicament to a patient is provided. The method may include providing an aerosolization system. The aerosolization system may include a respiration system comprising an inspiratory limb and an expiratory limb, an inlet coupled with the inspiratory limb of the respiration system, and an outlet coupled with the expiratory limb of the respiration system, wherein the outlet is in fluid communication with the inlet. The aerosolization system may also include an aerosol chamber coupled with one of the inlet or the outlet via a fluid channel. The fluid channel may be disposed such that the aerosol chamber is isolated from continuous flow passing from the inlet to the outlet. The aerosolization system may also include a patient interface positioned at a first end of the aerosol chamber and an aerosolization device positioned at a second end of the aerosol chamber opposite the first end. The aerosolization device may include a reservoir that is configured to receive a volume of liquid medicament for aerosolization by the aerosolization device. The aerosol chamber may be configured to mix aerosolized medicament from the aerosolization device with respiratory flow received from the respiration system via the fluid channel.

The method may also include interfacing the patient interface with a patient's airway and causing a respiratory flow to flow from the respiration system through the inlet and the outlet. The method may further include aerosolizing a volume of liquid medicament within the aerosolization chamber using the aerosolization device such that the aerosolized medicament mixes with a portion of respiratory flow that has been drawn into the chamber and delivering the mixture of aerosolized medicament and respiratory flow to the patient via the patient interface.

In one embodiment, an aerosolization device is provided. The device may include an aerosol chamber having a first end and a second end and an aerosol generator positioned at the first end of the aerosol chamber. The aerosol generator may be configured to aerosolize a volume of medicament into particles having a mass mean aerodynamic diameter (MMAD) of less than about 3 μm at a rate of at least 0.1 ml/min. The device may also include a patient interface that is positioned proximate the second end of the aerosol chamber and a respiratory adaptor that is configured to couple the aerosolization device with a respiration system and to divert a portion of airflow of the respiration system to the aerosol chamber via a fluid channel. The aerosol chamber may be configured to mix the portion of the airflow with aerosolized surfactant from the aerosol generator for subsequent delivery to a patient via the patient interface. In some embodiments, the aerosol generator may include a reservoir that is configured to receive a volume of liquid surfactant for aerosolization by the aerosol generator. In some embodiments, the respiratory adaptor may include a diversion mechanism that is configured to divert the portion of airflow from the respiration system into the aerosol chamber via the fluid channel. In some embodiments, the portion of airflow may be respiratory flow and is less than an amount of air that continues to an expiratory limb of the respiration system. In some embodiments, the diversion mechanism may include at least one baffle that defines the fluid channel. The at least one baffle may be configured to divert the portion of airflow into the aerosol chamber via the fluid channel and to divert an additional portion of airflow from an inspiratory limb to an expiratory limb. In some embodiments, the at least one baffle may include a first baffle that defines a first airway and a second baffle that defines a second airway. In some embodiments, the first airway is provided at a lateral end of the first baffle, the second airway is provided beyond a distal edge of the second baffle, and the lateral end and the distal edge extend in different directions such that the respiratory flow moves in multiple directions to pass the first baffle and the second baffle.

In some embodiments, the device may include a conduit that is configured to deliver the volume of medicament to the aerosol generator. A distalmost tip of the conduit has a diameter. The distalmost tip of the conduit may be positioned at a distance from the mesh that is less than or equal to the diameter. In some embodiments, the aerosol chamber may be generally funnel-shaped such that the first end comprises a wide portion of the aerosol chamber and the second end comprises a narrow portion of the aerosol chamber. In some embodiments, the patient interface may include nasal prongs. In some embodiments, In some embodiments, a fluid path defined by the fluid channel forms an angle of no greater than 90 degrees with an upstream side of a flow path through the respiration system. In some embodiments, the respiratory adaptor may include an inlet that is configured to interface with an inspiratory limb of the respiration system and an outlet that is configured to interface with an expiratory limb of the respiration system. In some embodiments, the fluid channel may be positioned such that the respiratory flow does not enter the aerosol chamber between breaths of the patient. In some embodiments, the device may include a fluid supply line coupled with aerosolization device and a pump configured to deliver the volume of medicament to a reservoir of the aerosolization device via the fluid supply line. In some embodiments, the medicament comprises a surfactant.

In another embodiment, an aerosolization device may include an aerosol chamber and an aerosolization generator positioned at a first end of the aerosol chamber. The aerosolization generator may be configured to aerosolize a volume of medicament into particles having a mass mean aerodynamic diameter (MMAD) of less than about 3 μm at a rate of at least 0.1 ml/min. The device may also include a patient interface positioned at a second end of the aerosol chamber that is opposite the first end, an inlet that is configured to couple with an inspiratory limb of a respiration system, an outlet that is configured to couple with an expiratory limb of the respiration system, and a fluid channel coupling the aerosol channel with at least one of the inlet and the outlet. The fluid channel may be disposed such that the aerosol chamber is isolated from continuous flow passing from the inlet to the outlet. The aerosol chamber may be configured to mix respiratory flow received from the respiration system via the fluid channel with aerosolized medicament from the aerosolization device.

In some embodiments, the aerosol chamber may be generally funnel-shaped such that the first end includes a wide portion of the aerosol chamber and the second end includes a narrow portion of the aerosol chamber. In some embodiments, the patient interface includes nasal prongs or a nasal mask. In some embodiments, a fluid path defined by the fluid channel forms an acute angle with an upstream side of the at least one of one of the inlet and the outlet with which the fluid channel is coupled. In some embodiments, the inlet and the outlet may be configured to direct a flow of gas from the inspiratory limb to the expiratory limb such that the respiratory flow does not enter the aerosol chamber between breaths of the patient. In some embodiments, the device may also include a fluid supply line coupled with aerosolization device and a pump configured to deliver a volume of liquid medicament to a conduit of the aerosolization device via the fluid supply line. In some embodiments, the inlet and the outlet are integrally formed.

In another embodiment, a method of delivering aerosolized medicament to a patient is provided. The method may include providing an aerosolization device, which may include an aerosol chamber, a respiratory adaptor, an aerosol generator positioned at a first end of the aerosol chamber opposite the first end, and a patient interface positioned at a second end of the aerosol chamber. The method may also include interfacing the patient interface with a patient's airway, interfacing the respiratory adaptor with a respiration system, and diverting a portion of airflow of the respiration system into the aerosol chamber using the respiratory adaptor as the patient inhales. The method may further include supplying a volume of liquid medicament to the aerosol generator, aerosolizing the volume of liquid medicament within the aerosolization chamber using the aerosol generator to generate particles having a mass mean aerodynamic diameter (MMAD) of less than about 3 μm at a rate of at least 0.1 ml/min that mix with the airflow that has been introduced into the chamber, and delivering the mixture of aerosolized medicament and the airflow to the patient via the patient interface.

In some embodiments, the method may also include sensing an inhalation of the patient using one or more breath sensors. In some embodiments, the aerosolization of the volume of liquid medicament may be triggered based on the sensed inhalation of the patient. In some embodiments, the aerosol chamber is generally funnel-shaped such that the first end includes a wide portion of the aerosol chamber and the second end includes a narrow portion of the aerosol chamber. In some embodiments, the airflow is drawn into the aerosol chamber by a vacuum created by an inhalation of the patient at the patient interface. In some embodiments, the respiratory adaptor comprises an inlet and an outlet and the aerosol chamber is coupled with at least one of the inlet or the outlet via a fluid channel. The fluid channel may be disposed such that the aerosol chamber is isolated from continuous flow passing from the inlet to the outlet.

BRIEF DESCRIPTION OF THE DRAWINGS

FIG. 6A is a cross-sectional view of the aerosolization device of FIG. 6.

DETAILED DESCRIPTION

Figure 1:
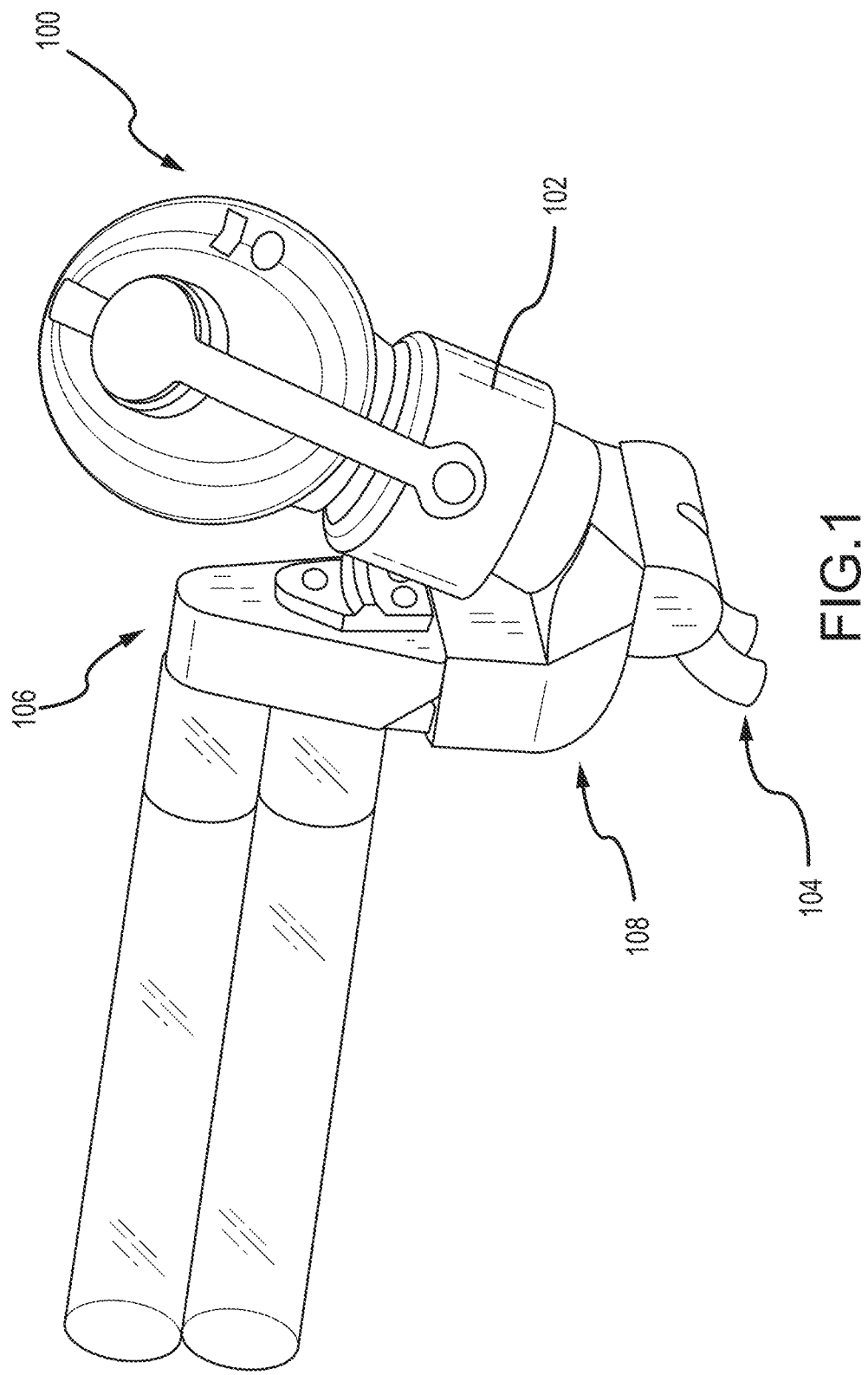
FIG. 1 is an isometric view of an aerosolization device according to embodiments.

The ensuing description provides embodiment(s) only, and is not intended to limit the scope, applicability or configuration of the disclosure. Rather, the ensuing description of the embodiment(s) will provide those skilled in the art with an enabling description for implementing an embodiment. It is understood that various changes may be made in the function and arrangement of elements without departing from the spirit and scope of this disclosure.

Embodiments of the invention provide aerosolization systems and methods in which aerosolized medicament and respiratory gases are mixed within an aerosolization chamber that is isolated from a direct flow of respiration system such that a small portion of the respiratory gases enter the aerosolization chamber while most of the respiratory flow bypasses the chamber and passes through an expiratory limb of a respiration system. Such design considerations ensure that drug delivery rates are consistent, regardless of flow rates from a respiration system. Additionally, embodiments of the invention provide retrofit aerosolization solutions that can be coupled with existing respiration systems to adapt the existing system to be able to deliver a reliable dose of aerosolized medicament to a patient's airways. Additionally, the aerosolization systems provided herein may include one or more breath sensors, such as one or more flow sensors, (e.g., electrical flow sensors), radar sensors (e.g., ultrawideband (UWB) radar sensors for measuring chest displacement), $CO_2$ sensors, high-speed temperature sensors, acoustic sensors, impedance plethysmography sensors, respiratory inductance plethysmography sensors, pressure sensors, and the like that enable a controller to predict a patient's inhalations, allowing for the aerosolization of medicament during, or immediately prior to, the patient's inhalations.

Embodiments of the invention provide aerosolization systems that isolate aerosolized medicament from a primary respiratory gas flow to avoid disruption and dilution of aerosol produced during inspiratory phase. Such isolation may be achieved using baffles and/or other barriers that are designed to redirect primary flow from inlet to outlet without flushing gas through the patient interface.

Embodiments of the invention also generate and deliver surfactant aerosol only during the inspiratory cycle (inhalation). Commonly used devices administer aerosol continuously. However, the infant can only inhale aerosol during inspiration, so during exhalation (up to two thirds of the breathing cycle) aerosol bypasses the airway and is lost and wasted. By limiting aerosol generation to occur only during inhalation and delivering the aerosol proximal to the nares, it can be assured that the highest percentage of surfactant is available for deposition in the lungs.

Embodiments of the invention also produce the aerosol proximate to a patient interface to help increase the amount of aerosol that is delivered to the patient. Conventional nebulizers are placed somewhere in the inspiratory tubing of the ventilator or nCPAP circuit, where aerosol is generated within a continuous flow of gas. This greatly dilutes the aerosol being delivered and much is lost in the continuous gas flow, which generally exceeds subjects inspiratory flow. In contrast, aerosolization devices of the present invention generate aerosol directly at the patient interface (such as nasal prongs) and diverts substantive gas flow from the nCPAP circuit away from the aerosol plume to markedly reduce aerosol loss in the continuous gas flow of the circuit. Embodiments also use an aerosol generator that emits aerosol surfactant at rates of 0.3 mL/min or greater with undiluted surfactant, which is faster than previously reported with other mesh nebulizers and reduces the time of administration. While discussed primarily in relation to the delivery of surfactant, it will be appreciated that other forms of medicament may be utilized with the aerosolization systems of the present invention to deliver aerosolized medicament to the lungs of a patient.

In some embodiments, the aerosolization systems described herein may include a reusable device controller and disposable single-patient single-use aerosolization device that includes a drug delivery circuit and/or breath sensor. Such aerosolization devices serve as stand-alone drug delivery devices that integrate with a variety of ventilation devices (such as CPAP devices), and in some embodiments is not designed to be connected to the hospital network or the Internet. For example, the controller may be a multi-patient, reusable component with flat panel touchscreen display, electronics, and software. The controller may have three core functions: to detect inspiration via a breath sensor (which may be designed for single patient use) that may be attached to a patient's abdomen, to advance suspension to the aerosolization device via an integrated feed mechanism, and to generate aerosol during inspiration at the nCPAP interface. These functions may occur in synchrony with the infant's inspiratory cycle. The flat panel touchscreen utilizes a graphical user interface (GUI) to allow the user to set and monitor delivery parameters, alarms, and system diagnostics. Visual and audible alarms may be integrated into the controller. A pod may be used to communicate the signal from the breath sensor to the controller, and communicate a signal to synchronize aerosol generation with the detected breaths. A reservoir from which the drug product is dispensed may be a drug vial in which medicament is provided.

In some embodiments, the disposable single-patient single-use aerosolization device includes a Vented Vial Access Device (VVAD) that facilitates access to the drug reservoir and is provided to the user in an individual package and a drug feed tubing that includes a luer connector (to VVAD) and tubing conveying drug suspension from the luer to the aerosol generator of the aerosolization device. The aerosolization device may also include an aerosol generator that may use a custom photo defined aperture plate (PDAP) vibrating mesh, which is unique in its ability to provide small droplet sizes and higher output rates. This is due to the PDAP mesh's innovative architecture, which provides up to 20-fold more apertures with smaller diameters than found in conventional meshes. The aerosol generator is designed to dispense aerosol proximal to the infant's airway and connect to conventional nCPAP systems.

The reusable controller is equipped with a built-in touch screen with processors that monitors delivery parameters, alarms (visual and audible) and system diagnostics. The controller and Pod work in concert to detect inspiration via a breath sensor attached on one end to the infant's abdomen and on the other end plugged into the pod. The controller activates the drug feed mechanism, which drives drug delivery to the nebulizer to breath-synchronize the aerosol generation to the infant's inspiratory cycle.

Lyophilized surfactant is reconstituted in its original glass vial to produce a saline/surfactant suspension. The vial is connected to the drug delivery circuit that includes drug feed tubing through a vented vial access device that punctures the vial septum allowing air to vent into the vial allowing suspension to empty in a consistent manner. The integral volumetric drug feed mechanism advances the surfactant suspension through the drug feed tubing and delivers it to the nebulizer (proprietary vibrating mesh) which is integrated into the drug delivery circuit interface. The interface uses nasal prongs. The interface is attached to the infant's clinical nCPAP circuit, and placed on the infant, replacing prior interface. Aerosol is then delivered in synchrony with the infant's inspiration triggered by the breath sensor.

While discussed largely in the context of surfactant, it will be appreciated that the methods and devices of the present disclosure may be used with any liquid medicament. For example, medicaments such as, but not limited to, bronchodilators, anti-infectives, anti-virals, anti-inflammatories mucokinetics, siRNAs, PFOB, and the like may be utilized in accordance with the present disclosure.

Turning to FIG. 1, one embodiment of an aerosolization system is provided. Here, an aerosolization device 100 is positioned on a first side of an aerosol chamber 102 with a patient interface 104 being positioned on an opposite, second side of the aerosolization chamber 102. The aerosolization device 100 may be a nebulizer or any other device that is configured to aerosolize a dose of liquid medicament. Such devices are described in U.S. Pat. Nos. 5,758,637, 6,235,177, U.S. Patent Publication No. 2015/0336115, and U.S. Patent Publication No. 2016/0130715, the entire contents of which are incorporated by reference herein. The aerosolization device 100 may include a reservoir that is configured to receive and/or house a quantity of liquid medicament to be aerosolized. In some embodiments, the reservoir may be a "virtual reservoir" in the form of a conduit that couples and extends between a fluid feed line and a mesh of the aerosolization device 100. For example, the conduit may be sized to only house between about 10-15 mcl that may collect within the conduit between aerosolizations. A primary reservoir may be in the form of a vial containing the medicament, which, via a feed mechanism and feedline, may provide the medicament to the mesh on a breath to breath basis via the conduit or virtual reservoir. In some embodiments, the patient interface may include nasal prongs, endotracheal tubes, nasal cannula/masks, tracheostomy tubes, and the like.

The system includes a respiratory adaptor 106 that is configured to interface with an artificial respiration system, such as a ventilator, humidifier, continuous positive airway pressure (CPAP) machine, nCPAP system, and/or combinations thereof. For example, the respiratory adaptor 106 may include an inlet 108, such as an inlet baffle, that is configured to couple with an inspiratory limb of a respiration system. For example, the inlet 108 may be an inlet baffle that is configured to couple with a Flexitrunk™ Midline Interface produced by Fisher & Paykel Healthcare and to direct respiratory flow into the aerosolization chamber 102. The inlet 108 may be coupled with the aerosol chamber 102, such as via a fluid pathway 110. In some embodiments, the inlet 108 is designed to redirect gas from the respiration system to the aerosolization chamber, without increasing resistance or work of breathing for the patient. This may be done by providing a fluid pathway 110 having a cross-sectional area that is about 80% or greater relative to an internal cross-sectional diameter of the patient interface 104.

Figure 1A:
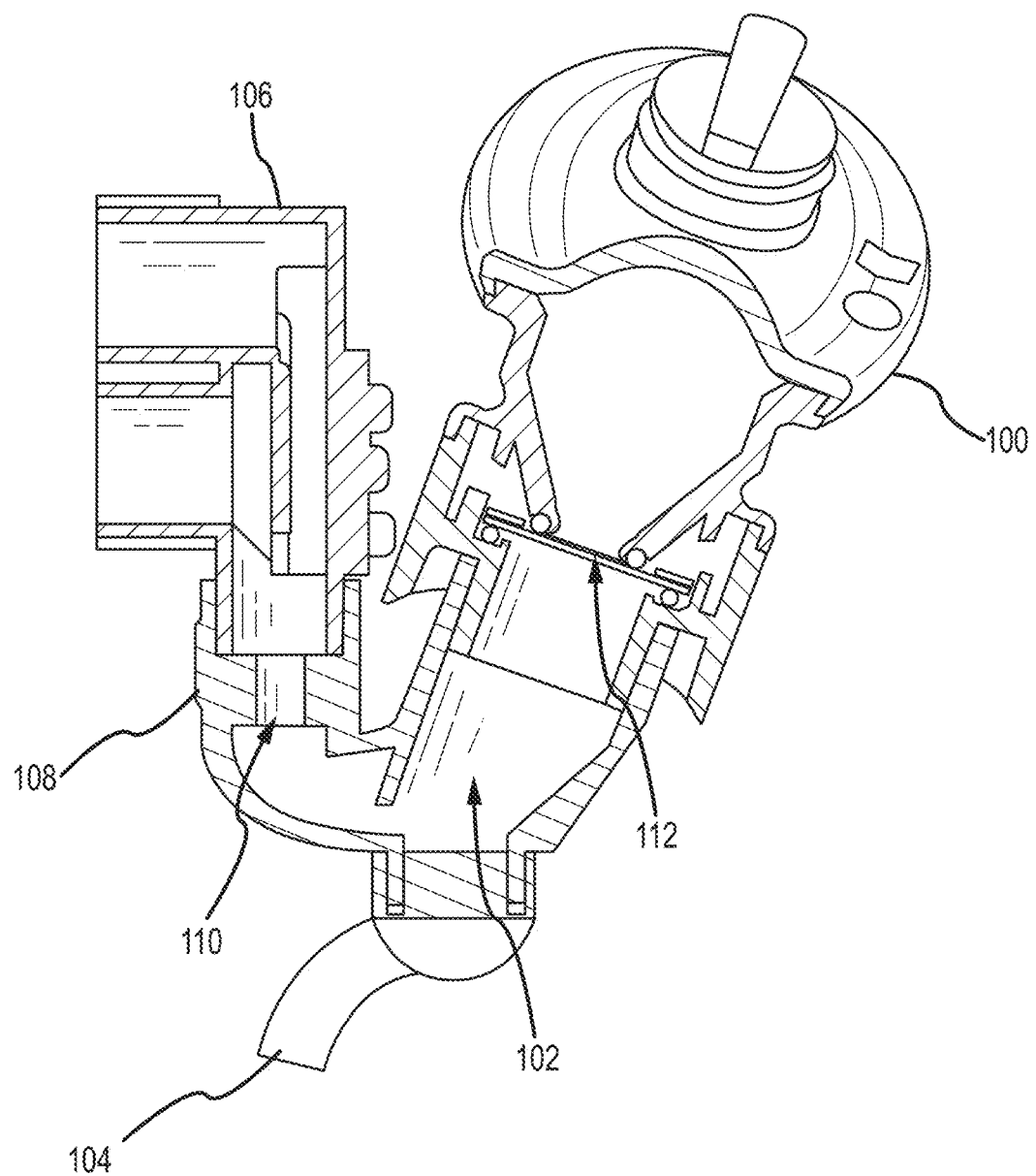
FIG. 1A is a cross-sectional view of the aerosolization device of FIG. 1.

FIG. 1A shows a cross-sectional view of the aerosolization system of FIG. 1. Here, an aerosol generator 112 of the aerosolization device 100 is shown positioned at the first end of the aerosol chamber 102 such that any medicament that is aerosolized by the an aerosol generator 112 is introduced into the aerosolization chamber 102. The aerosol generator 112 may include a mesh that is configured to generate aerosol particles. Conventional aerosol devices typically produce aerosol with mean droplet diameters in the 4 to 5 micron range. However, the aerosol droplet size requirement to deliver drug through the small airways of a premature infant's respiratory tract starting at the nares is generally less 3 microns in diameter. Aerosol droplets larger than this size are susceptible to either deposition in the nares and delivery tubing. If the droplets are much smaller than 1 micron the droplets may not deposit in the lungs and could be exhaled. This reduces the dose delivery efficiency to the lungs. Embodiments of the present invention utilize a mesh hole size that is designed to produce droplets with median diameters of between 2 and 3 microns. For example, in some embodiments, the aerosol generator 112 may include a Photo-defined aperture plate (PDAP) mesh that is configured to generate small aerosol particle sizes, such as below 3 µm. Such meshes are disclosed in U.S. Patent Publication No. 2016/0130715 which was previously incorporated by reference. Placement of the aerosol generator 112 proximal to the patient interface 104 allows aerosolized medicament emitted during inspiratory cycle to preferentially be inhaled with minimal disruption of continuous or bias flow passing through the respiration system circuit. Here, aerosol chamber 102 is shown with the first end being smaller than the second end. The inlet 108 is formed of a baffle that is designed to draw a portion of the respiratory flow from an inspiratory limb of a respiration system into the aerosol chamber 102 at a position near the first end via fluid pathway 110. The fluid pathway 110 is fluidly coupled with the inspiratory limb such that the fluid pathway 110 has an angle of no more than 90 degrees relative to the respiratory flow through the limb and/or an upstream side of the inspiratory limb at the junction between the limb and the inlet 108. Such positioning helps to isolate the aerosolization chamber from direct respiratory flow. For example, respiratory flow is introduced into the aerosol chamber 102 intermittently, occurring only during inhalations of the patient.

Figure 2:
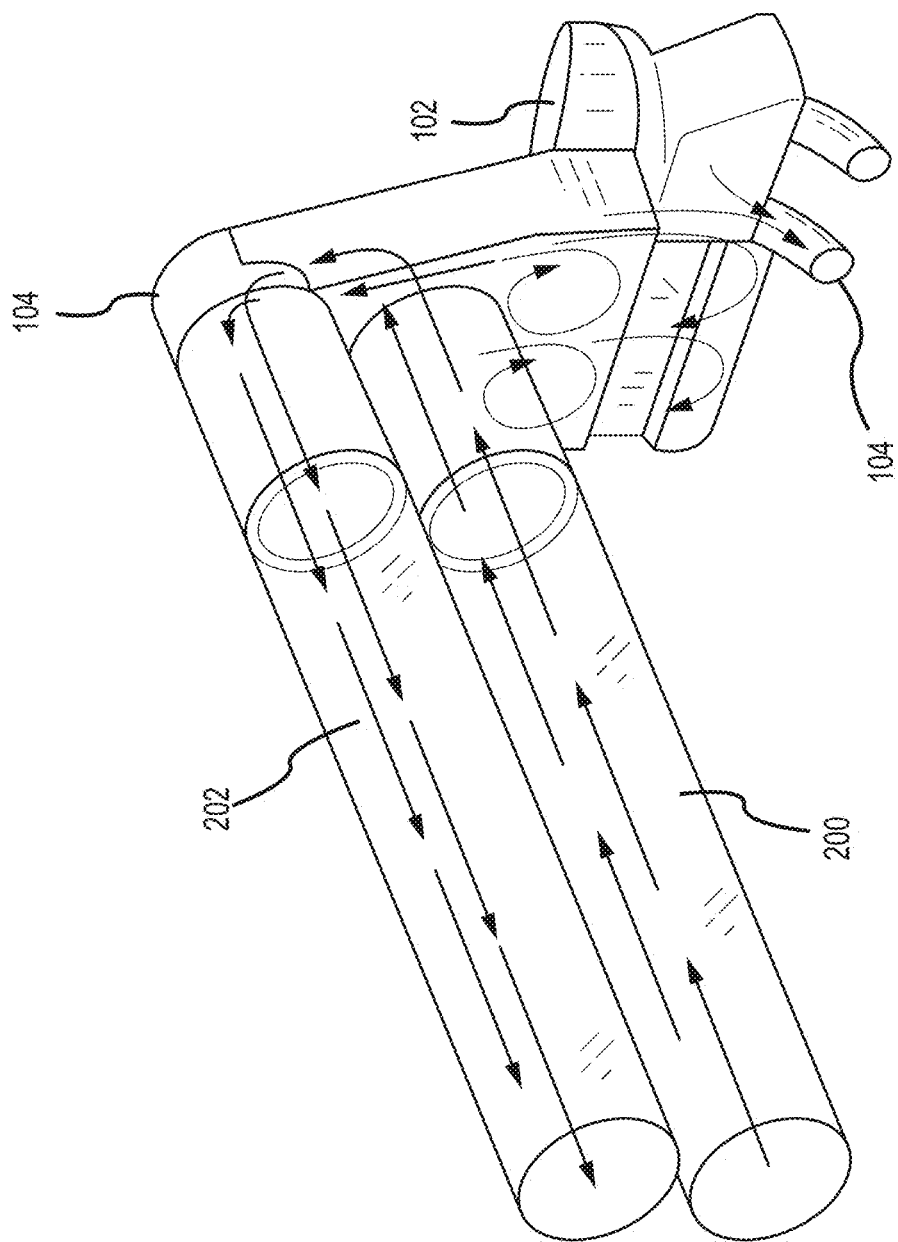
FIG. 2 illustrates flow patterns through the aerosolization device of FIG. 1.

Flow patterns through the aerosolization system are illustrated in FIG. 2, which shows an inspiratory limb 200 of a respiration system supplying respiratory airflow. A portion of this respiratory airflow may be drawn into the inlet 108 and introduced into the aerosol chamber 102 and patient interface 104 via the fluid pathway 110. For example, as the patient inhales, the inhalation creates a vacuum within the aerosolization chamber which draws in a volume of respiratory airflow through the fluid pathway 110. Excess respiratory airflow and/or exhaled gases may be expelled through an expiratory limb 202 of the respiration system.

The aerosolization system of FIGS. 1, 1A, and 2 provides higher and more consistent inhaled dose across a range of gas flows used with various nCPAP systems than conventional aerosolization systems. For example, the aerosolization systems described herein increase the inhaled dose with higher flow nCPAP systems (>6 L/min) from about 6% (as exhibited in conventional systems) to between about 40-50%, and reduced variability from low flow systems (0.5 L/min) which also deliver inhaled doses of between about 40-50%.

Figure 3:
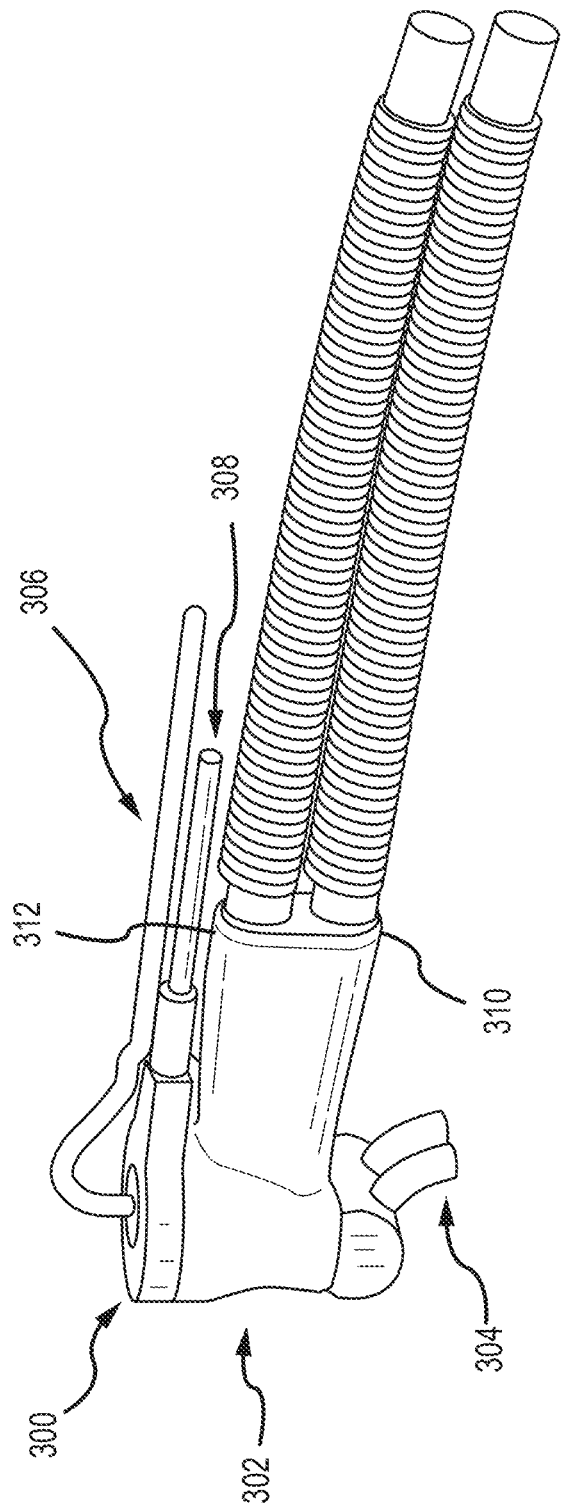
FIG. 3 is an isometric view of an aerosolization device according to embodiments.

FIG. 3 depicts another embodiment of an aerosolization device for providing consistent doses of aerosolized medicament to patients. The aerosolization device may include an aerosol generator 300 positioned at a first end of an aerosol chamber 302, with a patient interface 304 positioned at an opposite, second end of the aerosol chamber 302. The aerosol generator 300 may be a nebulizer having a vibratable mesh that is selectively vibratable using a piezoelectric actuator. In some embodiments, the aerosol generator 300 may include a reservoir that is configured to receive and/or house a volume of liquid medicament to be aerosolized. The aerosol generator 300 may be coupled to a medicament feed line 306 that is configured to deliver a volume of liquid medicament to the reservoir, such as via a pump (not shown). The aerosolization device may also include a cable 308 that is connected to a power source, although in some embodiments the aerosolization device may be battery powered.

In some embodiments, the aerosolization device may include an inlet 310 and an outlet 312 that may be respectively coupled to an inspiratory limb and an expiratory limb of an artificial respiration system. Potential artificial respiration systems include, but are not limited to, ventilators, humidifiers, CPAP machines, and/or combinations thereof. In some embodiments, the inlet 310 and outlet 312 may be a single unit forming a flow path for respiratory gases, while in other embodiments the inlet 310 and outlet 312 may be separate components that are coupled together. The inlet 310 and/or outlet 312 may be configured to receive ends of gas conduits of the respiration system. For example, inlet and/or outlet airflow baffles may support the one-way circuit of standard nCPAP circuits. This enables the baffles to minimize disruption of airflow from inlet to outlet resulting in less disturbance of the aerosol chamber 302.

Figure 3A:
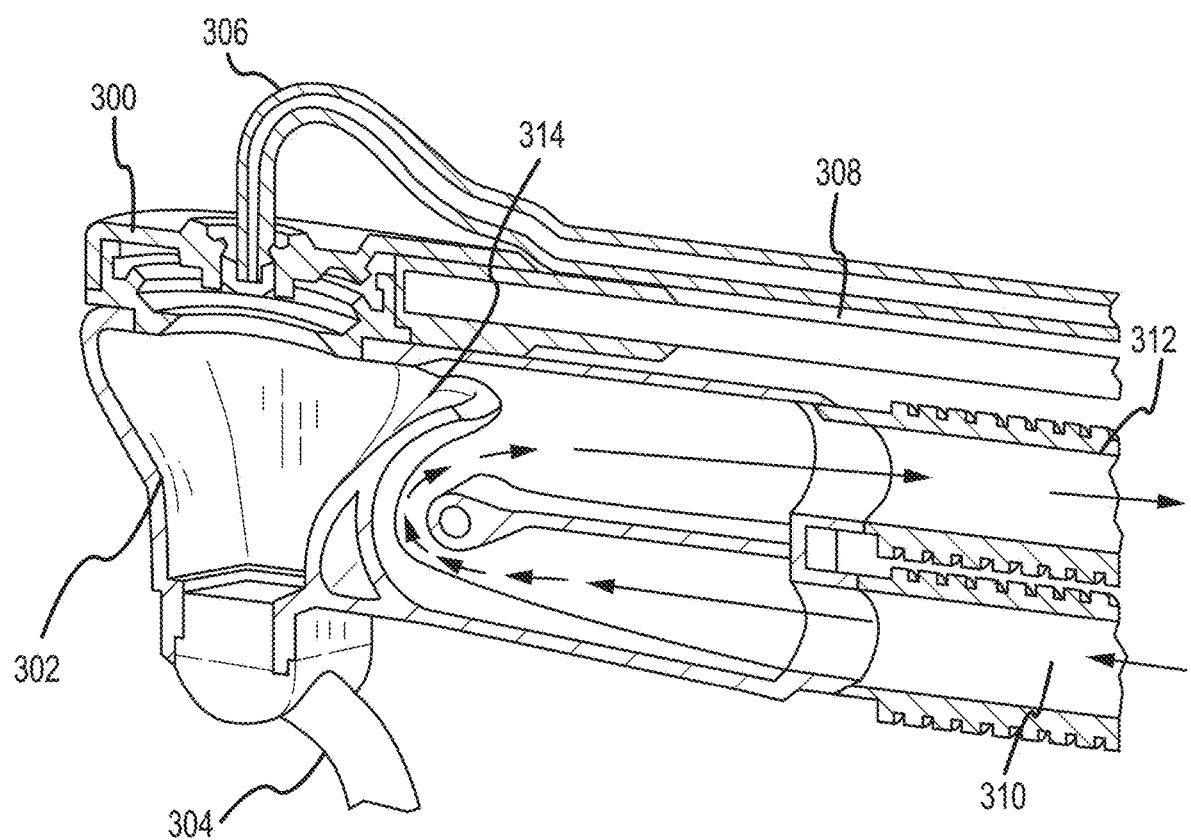
FIG. 3A is a cross-sectional view of the aerosolization device of FIG. 3.

As seen in FIG. 3A, the aerosolization device also includes a fluid flow path 314 that connects the aerosol chamber 302 with the inlet 310 and/or the outlet 312. As shown here, fluid flow path 314 may deliver respiratory gases to a top portion of the aerosol chamber 302 proximate the aerosol generator 300, although in some embodiments other locations, such as medial portions of the aerosol chamber 302 and/or portions proximate the patient interface 304 may be contemplated. Fluid flow path 314 may intersect with the inlet 310 and/or outlet 312 in such a manner that the fluid flow path 314 forms no greater than a 90 degree angle with an upstream side of the inlet 310 and/or outlet 312 and/or a flow path formed within the inlet 310 and/or outlet 312, such that the gas flow path 314 is orthogonal to the inlet 310 and/or outlet 312 or extends in a direction that at least partially opposing the flow of air though the inlet 31 and/or outlet 312. Such positioning of the fluid flow path 314 helps to isolate the aerosol chamber 302 from the continuous flow of the respiratory gases flowing from the inlet 310 (inspiratory limb) to the outlet 312 (expiratory limb). This provides several benefits. First, the isolation of the aerosol chamber 302 from the continuous flow prevents aerosolized medicament from being "whipped away" or diluted by the gas flow. Secondly, the isolation allows for the pre-loading of the aerosol chamber 302 with aerosolized medicament immediately prior to a breath event, while also enabling any medicament left over from a previous breath to be preserved.

In some embodiments, a portion of the respiratory gases may be drawn through the fluid flow path 314 and into the aerosol chamber 302 for mixing with aerosolized medicament. The portion of the respiratory gases that are drawn into the aerosol chamber 302 may be drawn in via the vacuum created by the patient inhaling at the patient interface 304.

Aerosol chamber 302 has an inner geometry that is optimized to direct plume towards the patient interface 304 with minimal impact action. Specifically, the aerosol chamber 302 is designed such the aerosol generator 300 is positioned opposite the patient interface 304. Additionally, the aerosol chamber 302 is designed with a generally funnel-shaped profile, which helps to reduce impaction when aerosol exits the aerosol generator 300 by providing a wider portion that tapers (linearly or nonlinearly) to a narrow portion proximate the patient interface 304. Such a design also helps to minimize the size of the aerosol chamber 302.

Figure 4A:
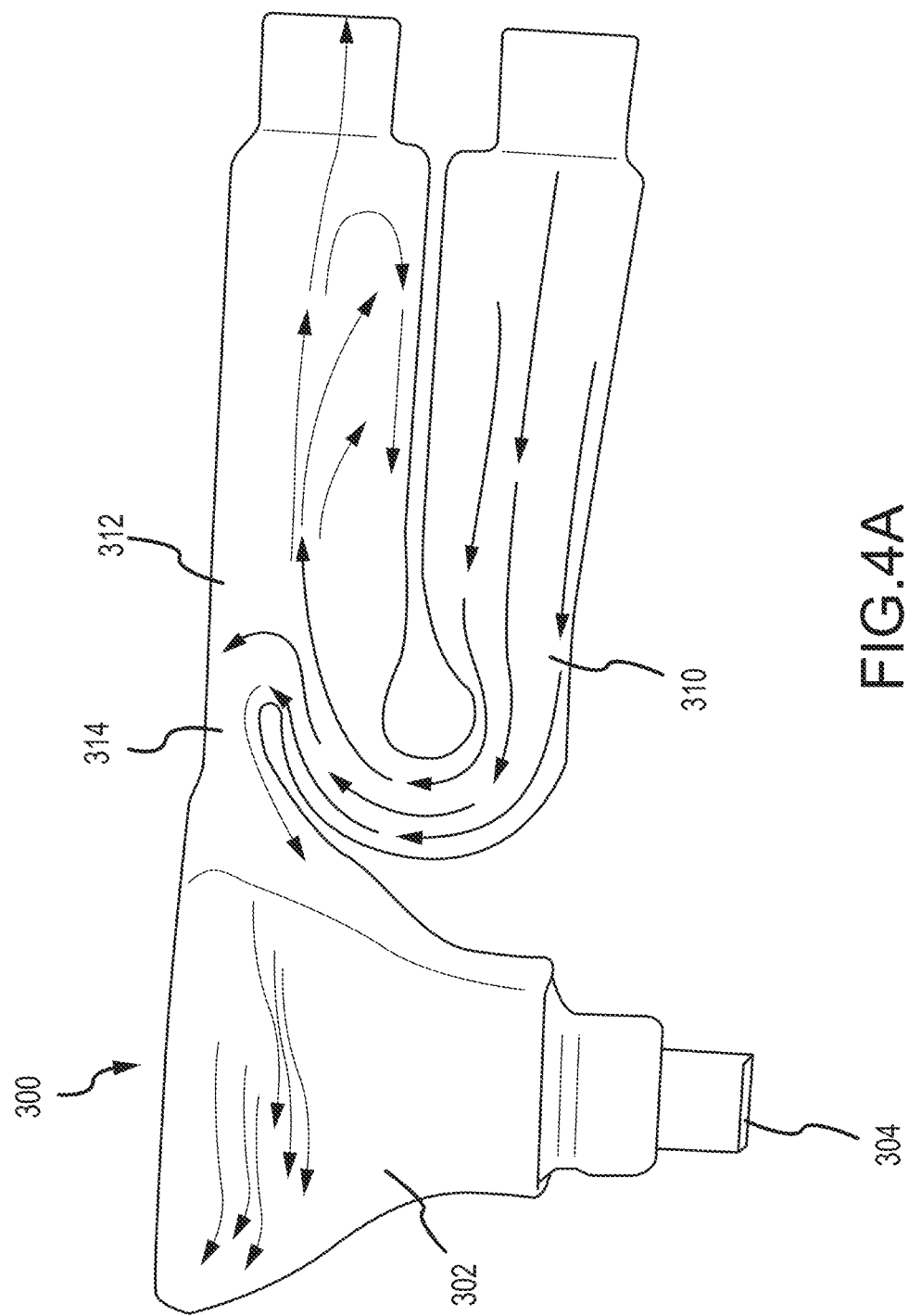
FIG. 4A illustrates flow patterns through the aerosolization device of FIG. 3.
Figure 4B:
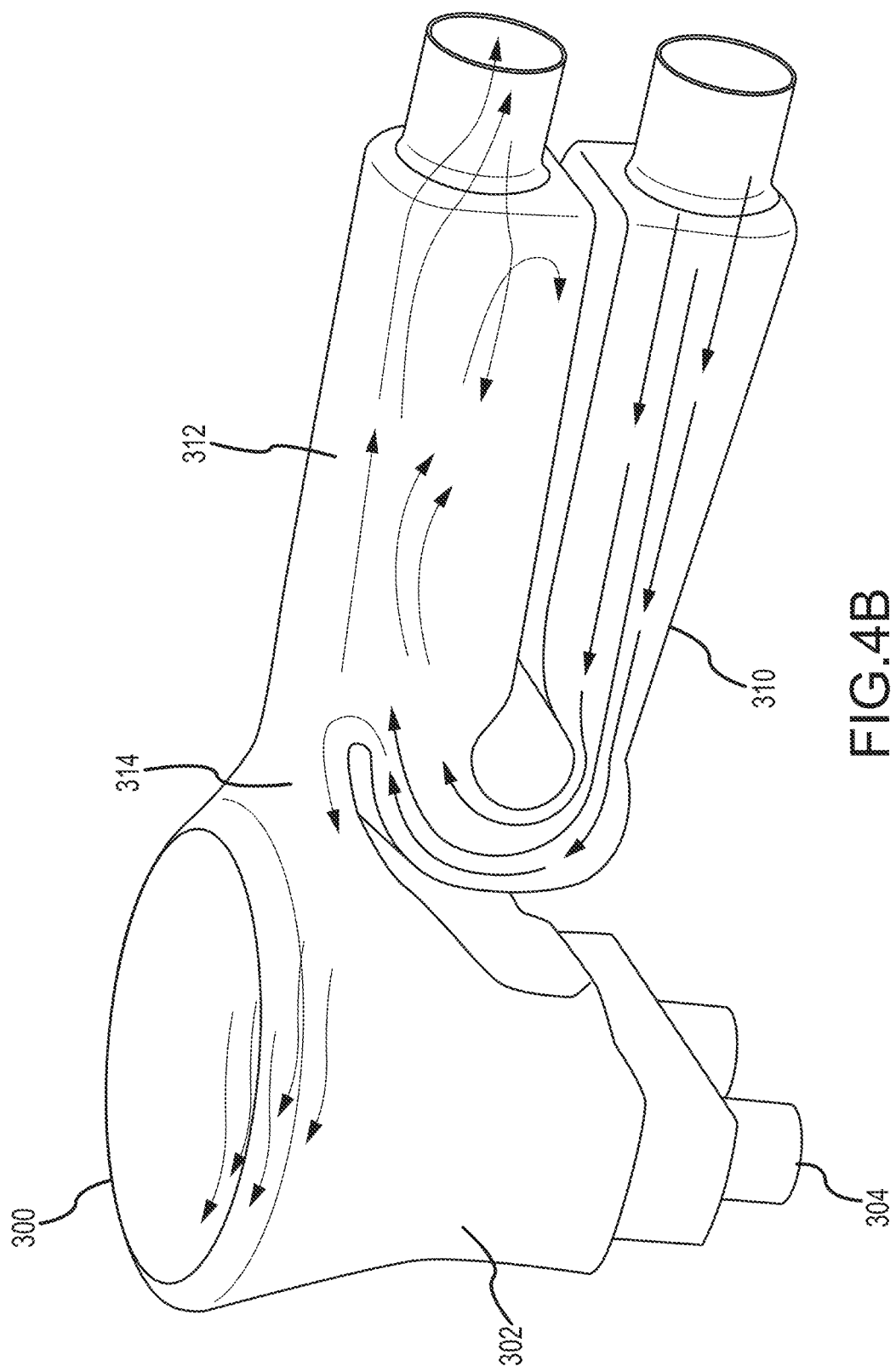
FIG. 4B illustrates flow patterns through the aerosolization device of FIG. 3.

FIGS. 4A and 4B depict flow paths of respiratory flow from a high flow respiration system through the aerosolization device of FIGS. 3 and 3A. Inspiratory flow is flowing through the inlet 310 at a rate of 8 L/min while the patient inhales at a rate of 1 L/min. Pressure at the expiratory limb coupled with the outlet 312 is 5 cm $H_2O$. A portion of the respiratory gases are drawn through fluid flow path 314 and into the aerosol chamber 302 as the patient inhales through the patient interface 304.

Figure 5A:
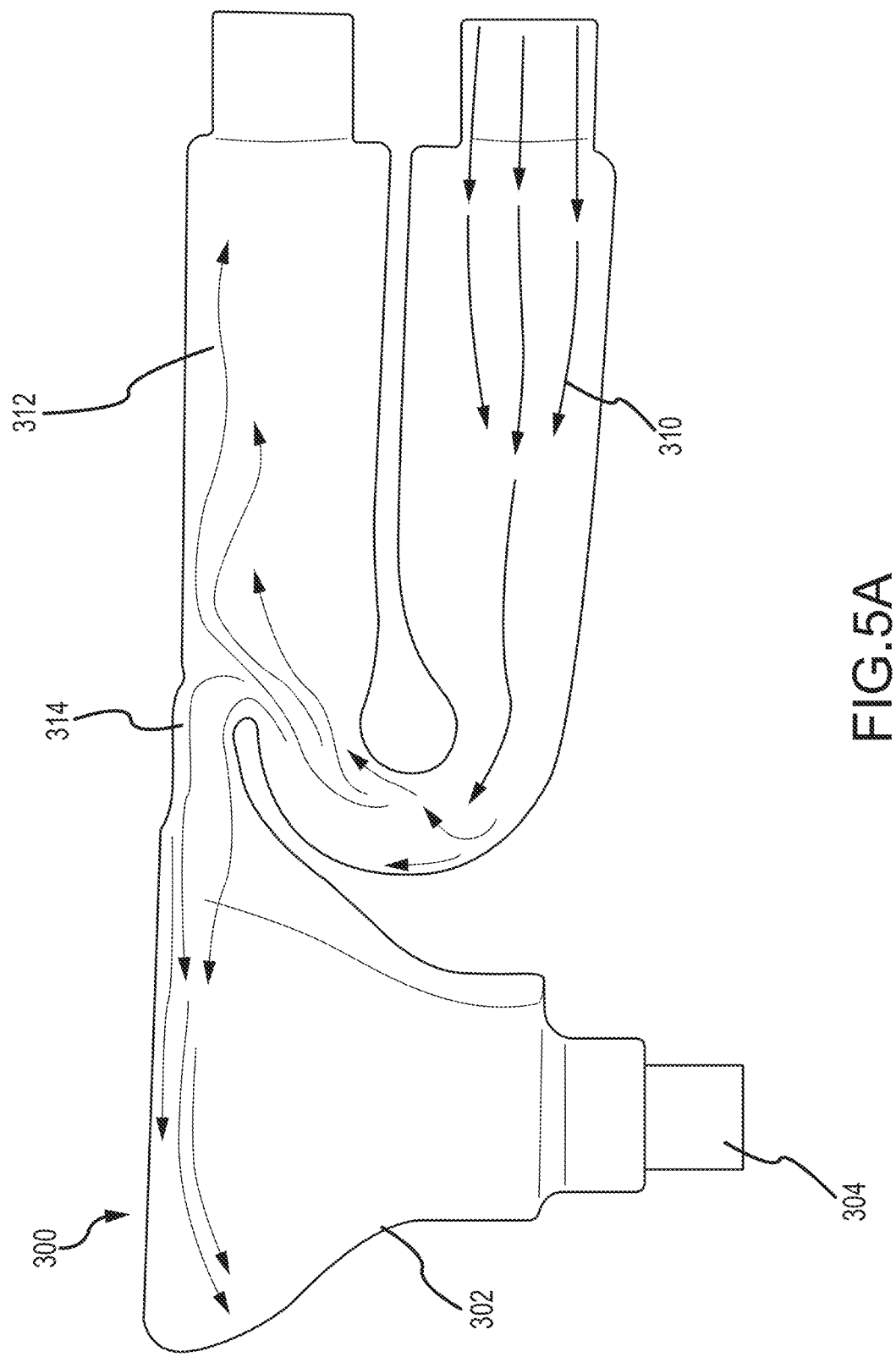
FIG. 5A illustrates flow patterns from a low flow respiration system through the aerosolization device of FIG. 3.
Figure 5B:
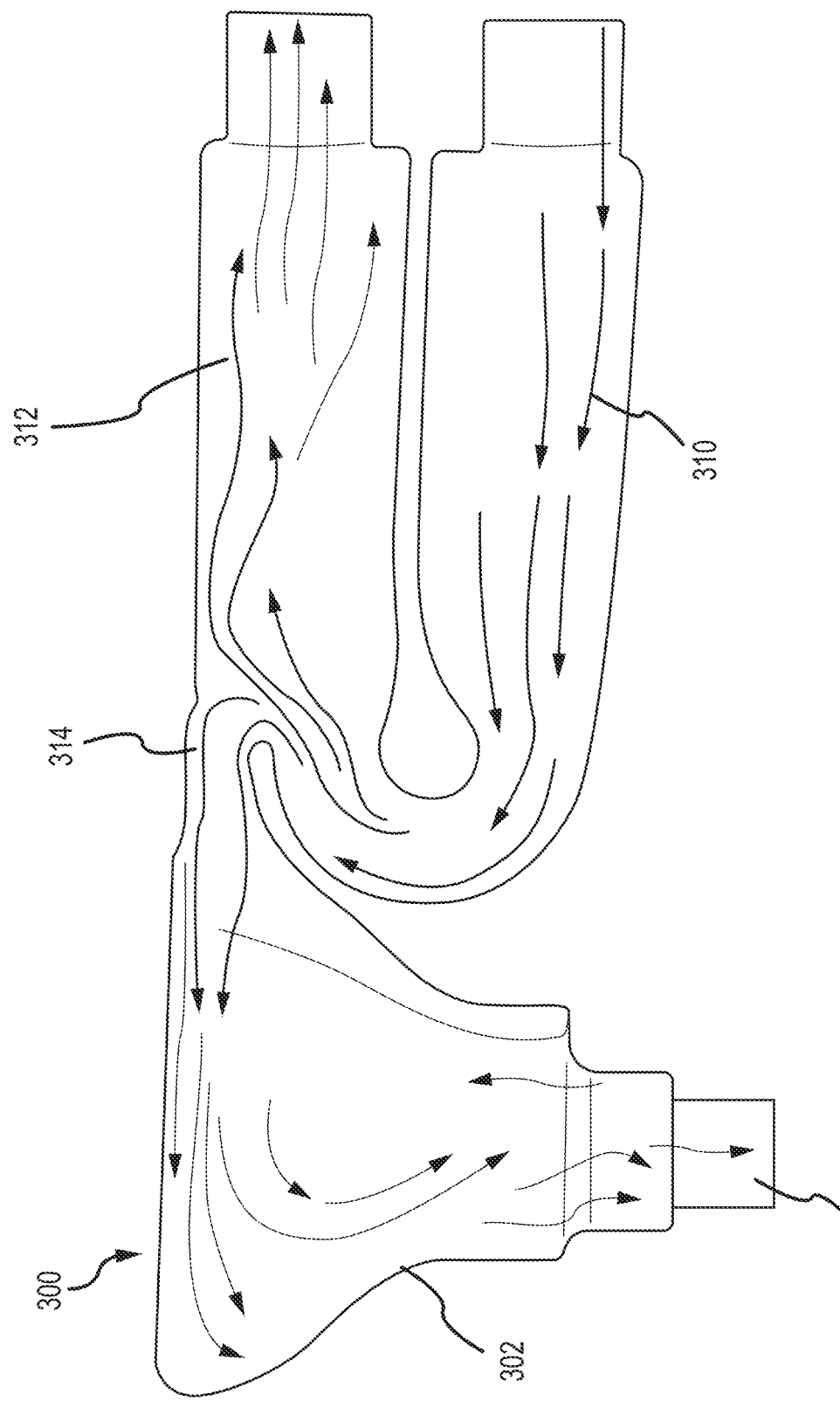
FIG. 5B illustrates flow patterns from a low flow respiration system through the aerosolization device of FIG. 3.

FIGS. 5A and 5B depict flow paths of respiratory flow from a low flow respiration system through the aerosolization device of FIGS. 3 and 3A. Inspiratory flow is flowing through the inlet 310 at a rate of 2 L/min while the patient inhales at a rate of 1 L/min. Pressure at the expiratory limb coupled with the outlet 312 is 5 cm H₂O. Similar to the high flow embodiment, a portion of the respiratory gases are drawn through fluid flow path 314 and into the aerosol chamber 302 as the patient inhales through the patient interface 304. As seen in FIG. 5B, the portion of respiratory flow that is drawn into the aerosol chamber 302 is introduced to the patient's airway via patient interface 304.

Figure 6:
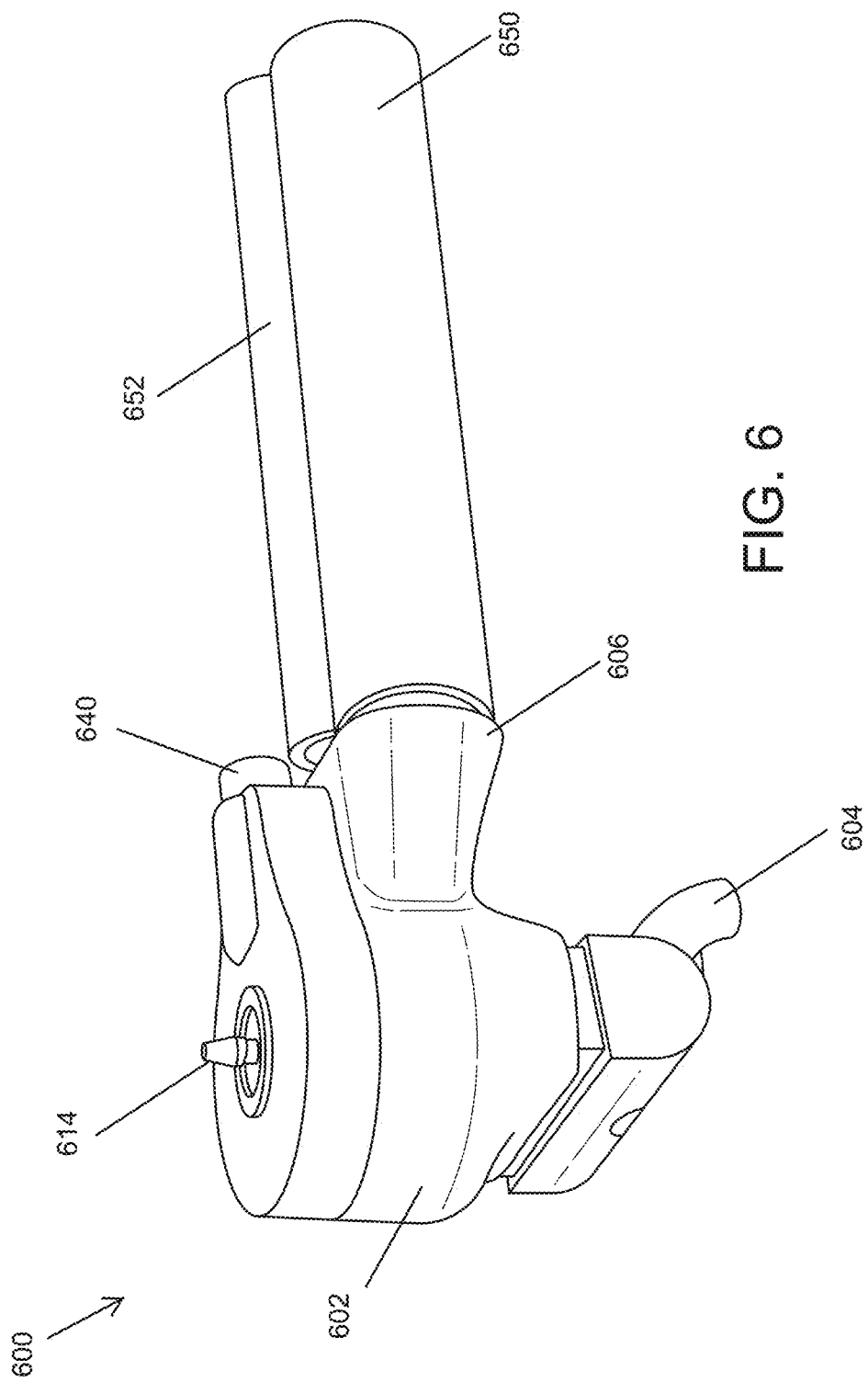
FIG. 6 illustrates an isometric view of an aerosolization device according to embodiments.
Figure 6B:
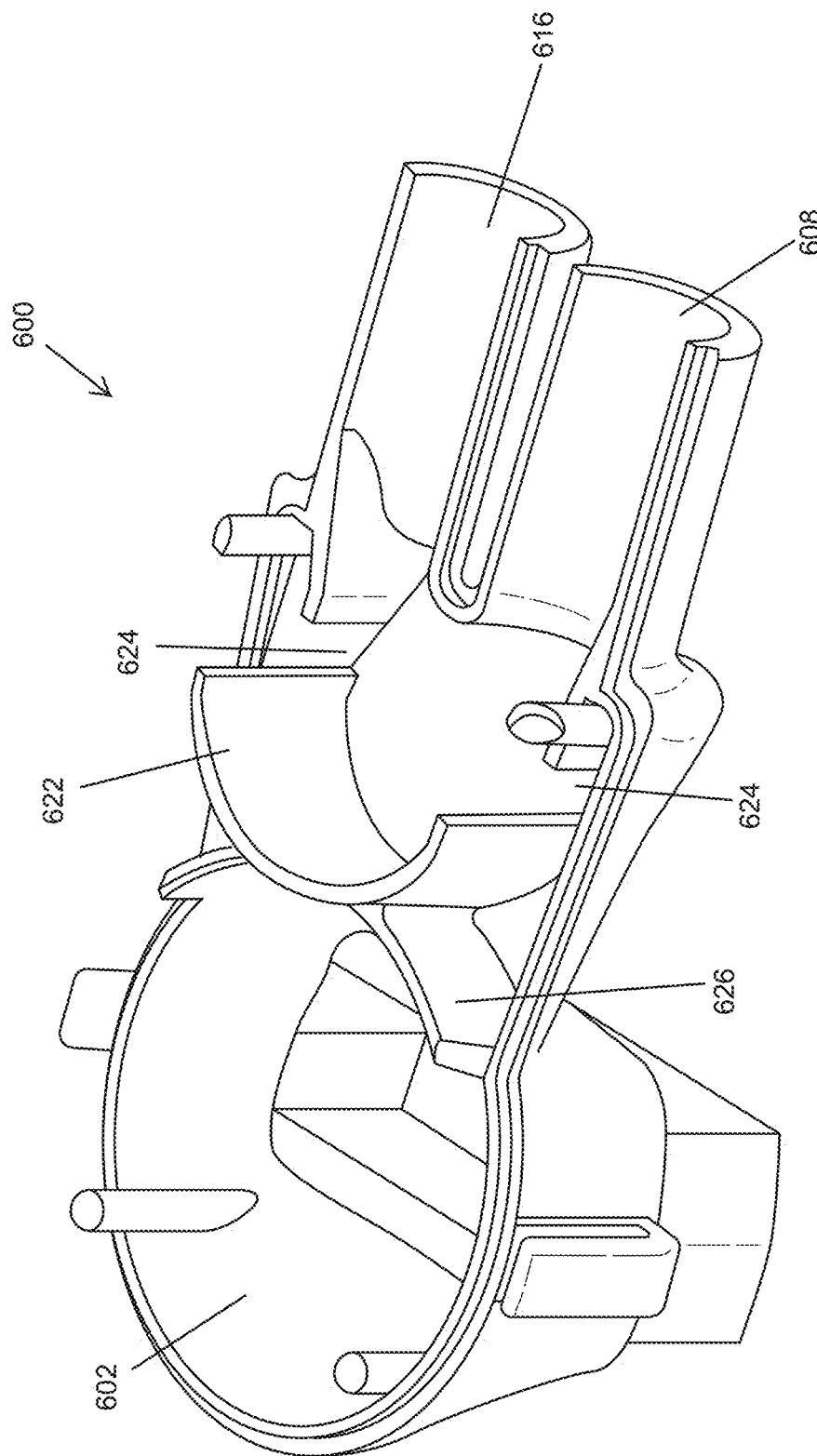
FIG. 6B is a cross-sectional view of the aerosolization device of FIG. 6.
Figure 6C:
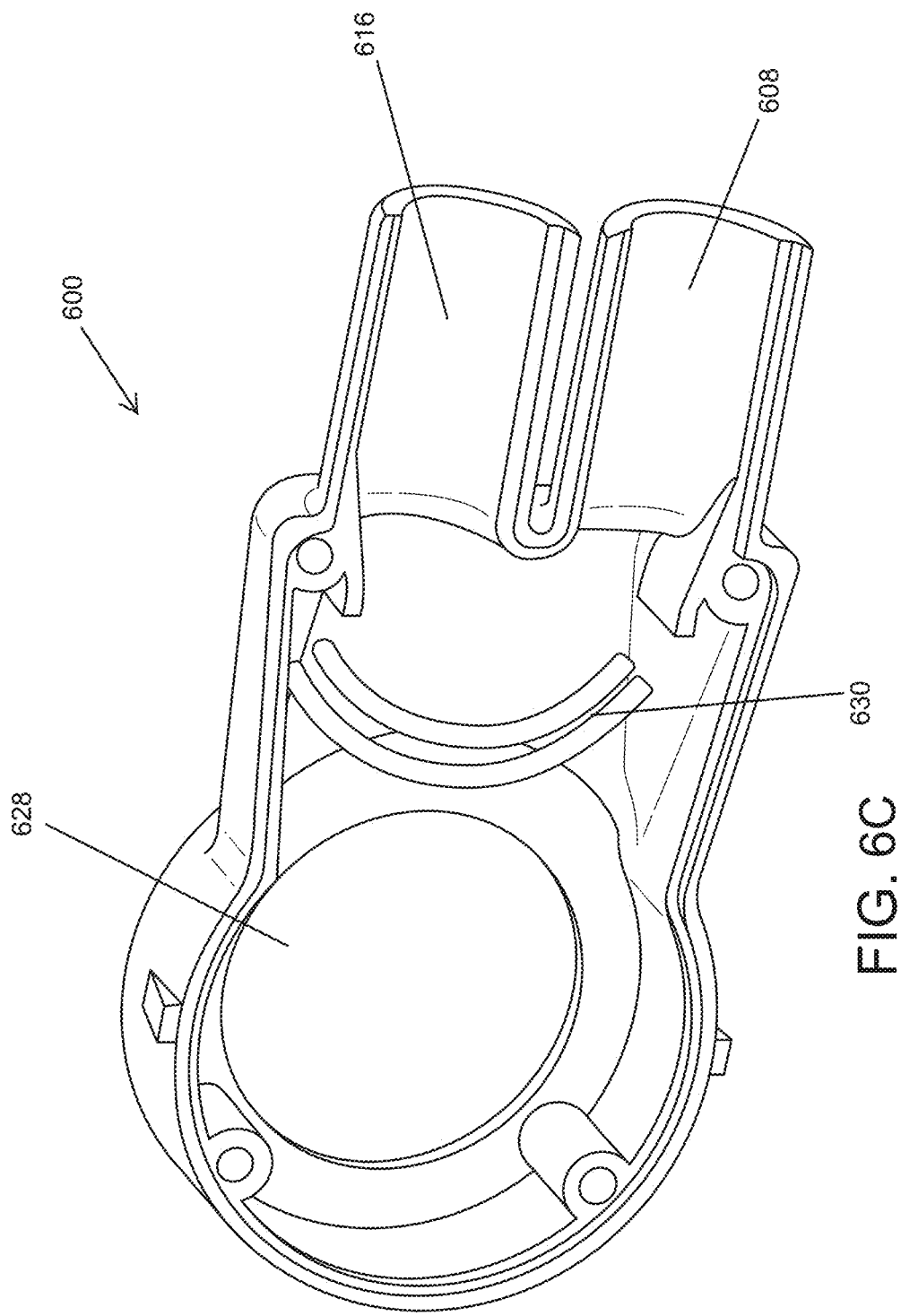
FIG. 6C is a cross-sectional view of the aerosolization device of FIG. 6.
Figure 6D:
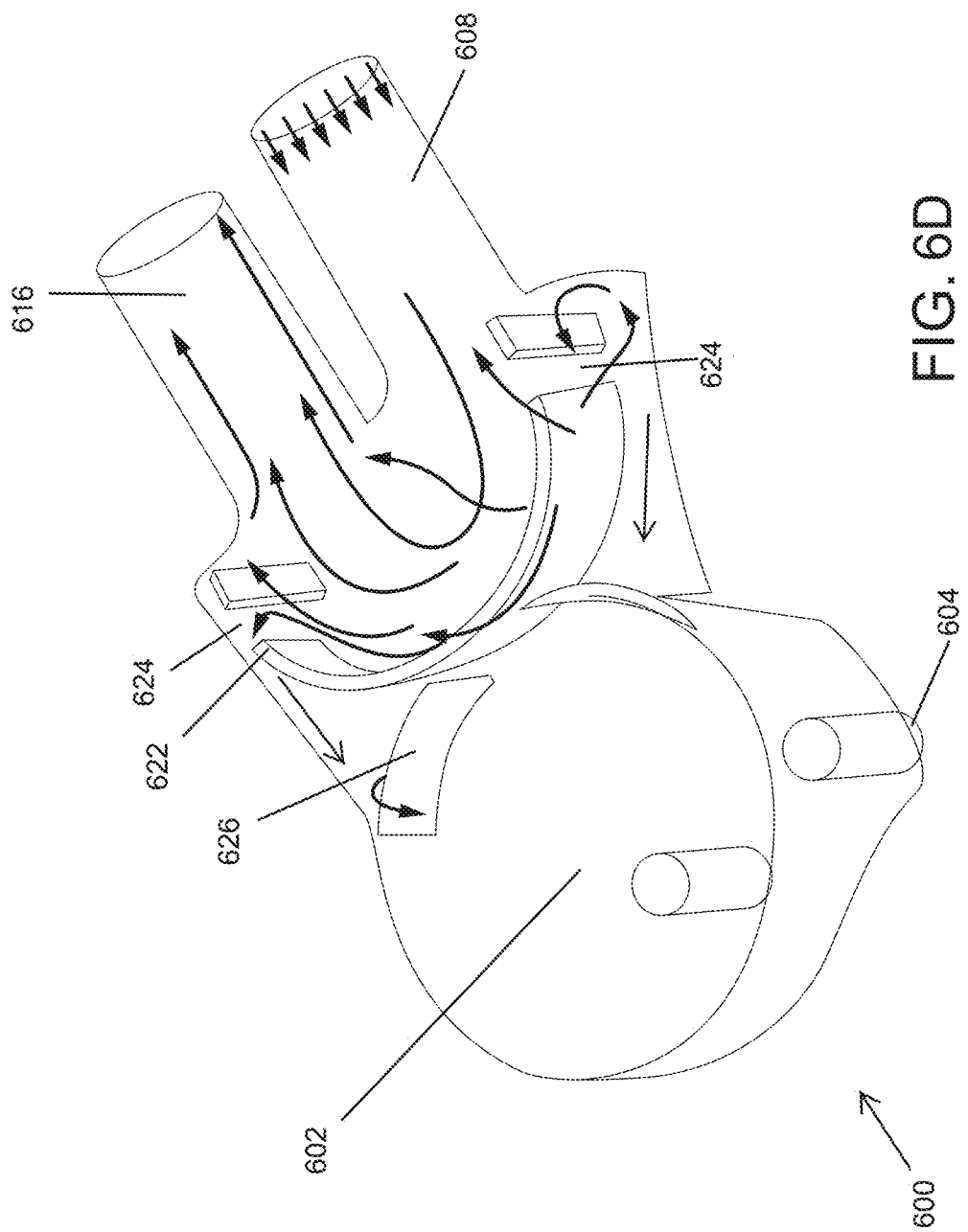
FIG. 6D illustrates flow patterns through the aerosolization device of FIG. 6.

FIGS. 6-6D illustrate another embodiment of an aerosolization device 600. Here, an aerosol generator 612 (shown in FIGS. 6A-6D), similar to those described above, is positioned on a first side of an aerosol chamber 602 with a patient interface 604 being positioned on an opposite, second side of the aerosol chamber 602. The aerosol generator 612 may include a reservoir that is configured to receive and/or house a quantity of liquid medicament to be aerosolized. For example, in some embodiments, the aerosolization device 600 may include at least one medication supply port 614 that is configured to be coupled with a medication supply line (not shown) that is used to deliver liquid medicament to the aerosol generator 612 (such as to the reservoir, if present). In some embodiments, the reservoir may be in the form of an elongate conduit that extends between the medication supply port 614 and the aerosol generator 612. In some embodiments, the patient interface 604 may include nasal prongs, endotracheal tubes, nasal cannula/masks, tracheostomy tubes, and the like. The aerosolization device 600 may also include at least one power connection 640. As illustrated, power connection 640 is a port that allows a power cable to be connected to the aerosolization device 600 to supply power and/or control commands to the aerosol generator 612.

The device includes a respiratory adaptor 606 that is configured to interface with an artificial respiration system, such as a ventilator, humidifier, continuous positive airway pressure (CPAP) machine, nCPAP system, and/or combinations thereof. For example, the respiratory adaptor 606 may include an inlet 608, such as an inlet baffle, that is configured to couple with an inspiratory limb 650 of a respiration system. The respiratory adaptor 606 may also include an outlet 616, such as an outlet baffle, that is configured to interface with an expiratory limb 652 of a respiration system. For example, as illustrated the inlet 608 and/or outlet 616 may be configured to be inserted and retained (such as using a friction fit and/or other securement mechanism) within a conduit of the inspiratory limb 650 and expiratory limb 652, respectively. In other embodiments, the inlet 608 and/or outlet 616 may be configured to be larger than the conduits of the respirations system such that conduits of the inspiratory limb 650 and/or expiratory limb 652 may be inserted and retained (such as using a friction fit and/or other securement mechanism) within the inlet 608 and outlet 616, respectively. It will be appreciated that other techniques for interfacing the inlet 608 and/or outlet 616 with a respiration system may be utilized and that the inlet 608 and outlet 616 need not be interfaced using the same techniques.

FIG. 6A shows a cross-sectional view of the aerosolization system of FIG. 6. Here, the aerosol generator 612 of the aerosolization device 600 is shown positioned at a first end 618 of the aerosolization chamber 602 such that any medicament that is aerosolized by the aerosol generator 612 is introduced into the aerosol chamber 602. For example, the medicament may be delivered to the aerosol generator 612 via the medication supply port 614, which is in communication with a reservoir. In some embodiments, the reservoir may be a "virtual reservoir" in the form of a conduit 632 that delivers the medicament to a surface of the aerosol generator 612. The virtual reservoir, conduit 632, may be coupled with a medicament source, such as a vial, via a fluid line that is coupled with the medication supply port 614. A distalmost tip 634 of the conduit 632 may have a diameter that is less than or equal to the distance between the tip 634 and a proximal surface of a mesh of the aerosol generator 612. Such dimensioning ensures that drops of liquid medicament ejected from the tip 634 are sufficiently large to contact and transfer to the mesh of the aerosol generator 612. Surface tension ensures that the liquid stays on and spreads out along a surface of the mesh such that all or substantially all of the liquid is aerosolized. This allows the aerosolization device 600 to be operated in any orientation, allowing the patient (such as an infant) to be treated while on their side, back, or stomach. For example, in some embodiments, a tip of the medication supply port 614 may be positioned between about 5-40 microns from a surface of the aerosol generator 612, while the tip 364 has a diameter that is less than or equal to this distance. As illustrated, the aerosol generator 612 is placed proximate to the patient interface 604, as the only component separating the aerosol generator 612 from the patient interface 604 is the aerosol chamber 602. Such placement of the aerosol generator 612 proximate to the patient interface 604 allows aerosolized medicament emitted during inspiratory cycle to preferentially be inhaled with minimal disruption of continuous or bias flow passing through the respiration system circuit. Here, aerosol chamber 602 is shown with the first end 618 being smaller than a second end 620, which helps to reduce impaction when aerosol exits the aerosolization device 600.

The inlet 608 may be formed of a baffle that is designed to draw a portion of the respiratory flow from the inspiratory limb 650 of the respiration system into the aerosol chamber 602 at a position near the first end via a fluid pathway that will be described in greater detail in relation to FIGS. 6B and 6C. In some embodiments, the inlet 608 may be designed to redirect gas from the respiration system to the aerosol chamber 602, without substantially increasing resistance or work (e.g. inspiratory pressure) of breathing for the patient, or at least to any significant degree. This may be done by providing a fluid pathway in the respiratory adaptor 606 that includes a number of baffles that direct a portion air from the inspiratory limb (only enough for inspiration) into the aerosol chamber 602 in a manner that significantly reduces turbulence in the airflow that is drawn into the aerosolization device 600, thereby creating a more laminar flow within the aerosol chamber 602.

FIGS. 6B and 6C illustrate two halves of aerosolization device 600. While illustrated as being two separable components, it will be appreciated that aerosolization device 600 may include any number of components that may be coupled together (such as using connecting/mating features) and/or may be formed from a single component, which may be formed from known molding, 3D printing, and/or other manufacturing techniques, both known and unknown. As shown in FIG. 6B, a portion of the aerosolization device 600 that includes the fluid flow path including a number of baffles. In the illustrated embodiment, aerosolization device 600 includes a first baffle 622 that directs a significant amount of the flow from the inspiratory limb 650 to the expiratory limb 652, while allowing a portion of the flow from the inspiratory limb 650 to enter the aerosol chamber 602. For example, the baffle 622 may be generally U-shaped, with one or both ends being open to form airways 624 between the baffle 622 and the sidewalls of a housing of the aerosolization device 600 that allow a small amount of air to flow past the ends of the baffle 622, while a body of the baffle 622 prevents the remaining air from getting past the baffle 622 and instead directs the air into the expiratory limb 652. It will be appreciated that while a U-shaped baffle 622 is used in the present embodiment, other shapes may be used to meet the needs of a particular application.

The aerosolization device 602 may include a second baffle 626 that is positioned proximate the baffle 622. As illustrated, the second baffle 626 is in the form of a generally U-shaped barrier that is oriented in an opposite direction as baffle 622 (although other shapes and orientations of second baffle 626 are possible, such as a second baffle 626 that extends across a width of the interior of the aerosolization device 600 in a generally linear fashion and/or a second baffle that curves or is otherwise oriented in a same direction as baffle 622). In some embodiments, the first baffle 622 and the second baffle 626 may be a single component, such as by sharing a medial portion, while other embodiments utilize baffles that are separate components. As shown, second baffle 626, extends all the way to the sidewalls of the housing, but leaves a gap between a distal edge of the second baffle 626 and a top portion of the housing of the aerosolization device 602 that provides a pathway for air to enter the aerosolization chamber 602. Thus, as illustrated, as a patient inhales at the patient interface 604, a portion of the gases supplied by the inspiratory limb 650 are drawn through the airways 624 on one or more ends of the baffle 622, where the air is forced upward over the second baffle 624 and forms a generally laminar flow within the aerosol chamber 602. It will be appreciated, however, that in some embodiments rather than directing the airflow toward a top of the housing, the second baffle 626 may direct air to a bottom of the housing and/or to a central opening formed between a top and bottom baffle. Any number of designs of baffles and/or other diversion mechanisms (including valves) may be used to help isolate the aerosol chamber 602 from the direct flow of respiratory gases of the respiration system, while providing some flow of respiratory gases during inhalation of the patient.

FIG. 6C illustrates another portion of the aerosolization device 600 that interfaces with the first portion. This portion of the aerosolization device 600 defines a seat 628 for receiving the aerosol generator 612, medicament supply port 614, and/or other related components. A mating feature 630 may also be provided that receives and secures the baffle 622 in place. For example, the mating feature 630 may define a groove or channel that is sized and shaped to receive a top edge of the baffle 622. This connection ensures that the baffle 622 may extend all the way from a bottom surface of the housing of the aerosolization device 600 to a top surface of the housing, which ensures that only airflow through airways 624 on either end of the baffle 622 is permitted to pass beyond the baffle 622 while directed a substantial portion of the airflow to the outlet 616.

FIG. 6D illustrates a flow pattern for airflow that is drawn into the aerosolization device 600 via inlet 608 from the inspiratory limb 650. For example, air from the inspiratory limb 650 (which may pass through a humidifier), may pass through the respiratory adaptor 606, where the baffle 622 redirects a significant portion of the air into the expiratory limb 652 via the outlet 616. As described above, the baffle 622 provides one or more airways 624 that allow a portion of the airflow from the inspiratory limb 650 to be drawn inward on each inhalation of the patient. This portion of the air is drawn in through the airways where it encounters the second baffle 626. The second baffle 626 forces air that is drawn past the ends of the baffle 622 upward, where the air flows over the second baffle 626 and into the aerosolization chamber 602. As illustrated here, the air is introduced into the aerosol chamber 602 at a position near the first end 618 proximate the aerosol generator 612. In other embodiments, the airflow may be introduced into the aerosol chamber 602 at other locations. As just one example, the air may be introduced near sidewalls of the aerosol chamber 602 using a baffle similar to baffle 622. As illustrated here, the air is introduced into the aerosolization chamber 602 as a position near the first end 618 proximate the aerosol generator 612. In other embodiments, the airflow may be introduced into the aerosolization chamber 602 at other locations. As just one example, the air may be introduced near sidewalls of the aerosolization chamber 602 using a baffle similar to baffle 622. It will be appreciated that other designs and/or locations of baffles may be utilized to introduce air to the aerosolization chamber 602 while isolating the aerosolization chamber 602 from direct flow within the respiration system. Additionally, some embodiments may utilize other mechanisms to divert some air from the respiration system into the aerosolization chamber 602 during each inspiration of the patient. For example, some embodiments may incorporate one or more one-way valves that are disposed between the aerosolization chamber 602 and the inspiratory limb 650 and/or expiratory limb 652. The one or more valves seal off and/or otherwise isolate the aerosolization chamber 602 from the respiration system until the patient breathes in, at which time the one or more valves open and allow a small volume of respiratory flow into the aerosolization chamber 602.

By using a series of baffles that direct small amounts of air from the inspiratory limb 650 into the aerosol chamber 602, embodiments of the present invention ensure the air drawn into the aerosol chamber 602 may be less turbulent and more laminar, which provides better deposition of medicament within the lungs. The baffles may be designed so that the gas/air that is drawn past the baffles is at or near the inspiratory flow of infants (which is much lower than gas passing through the inspiratory limb 650. It will be appreciated that while two baffles are used in the illustrated embodiments, other numbers and arrangements of baffles may be utilized to reduce the turbulence within the airflow from the inspiratory limb 650 prior to introducing the airflow into the aerosol chamber 602 without providing a significant increase to the amount of inhalation force needed to draw air into the patient's airways. Additionally, while shown with U-shaped baffles it will be appreciated that other baffle designs may be used that both limit the amount of airflow that is drawn into the aerosol chamber 602 during each inhalation and reduce the amount of turbulence within such airflow. This also helps reduce the dilution of the aerosolized medicament in the air supplied by the inspiratory limb 650.

Figure 7:
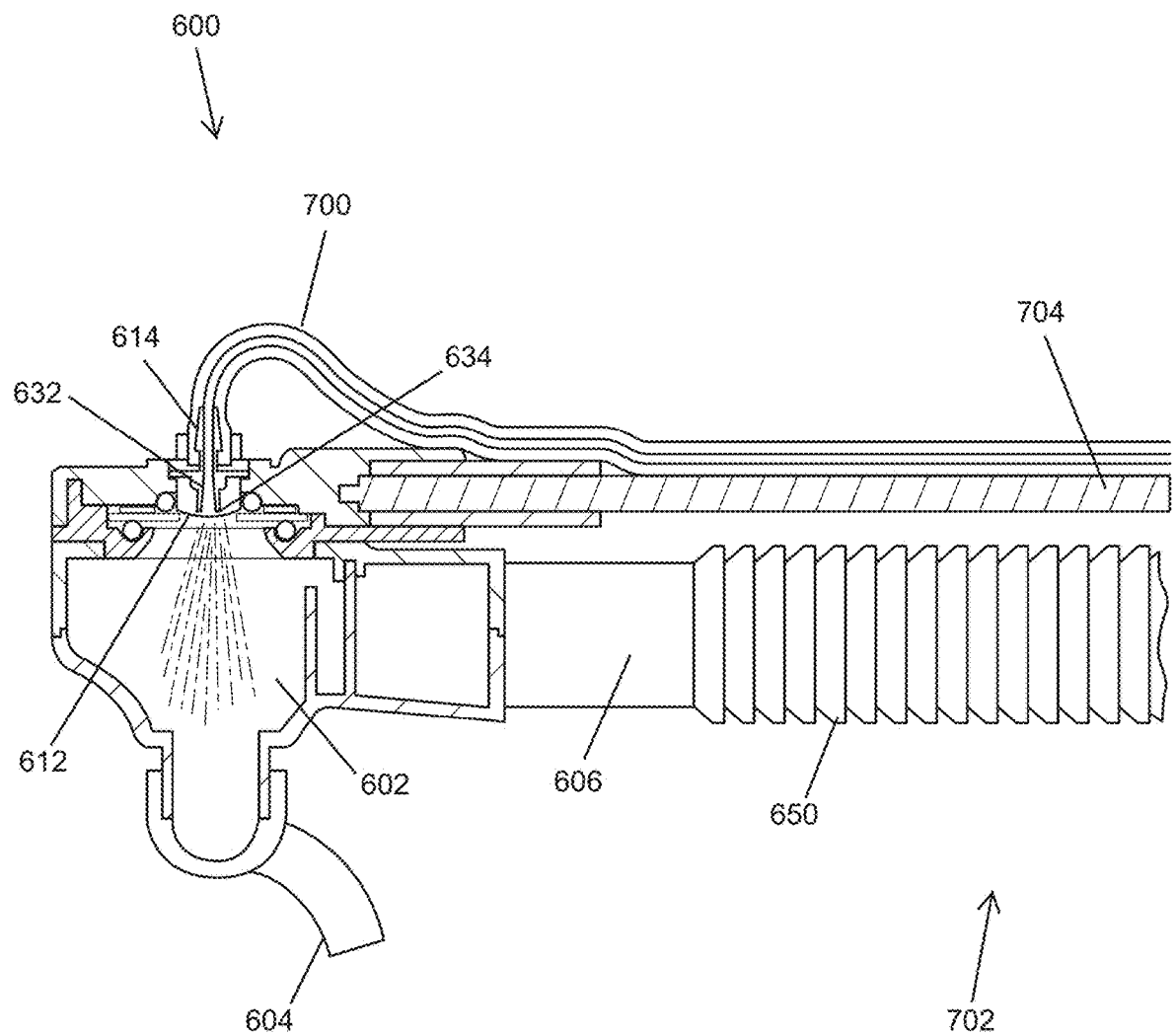
FIG. 7 illustrates the aerosolization device of FIG. 6 connected with a fluid supply line and a respiration system.
Figure 8:
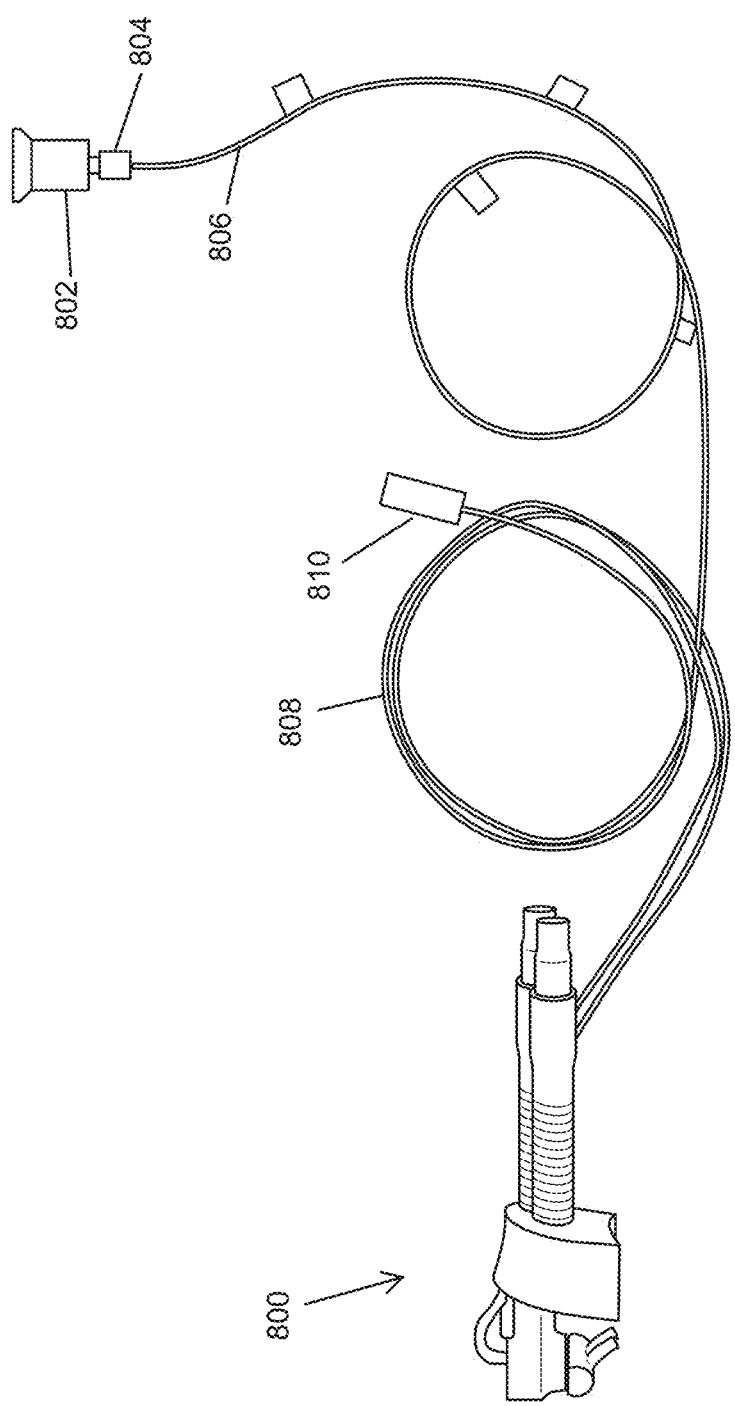
FIG. 8 illustrates an aerosolization device connected with a medication source.
Figure 9:
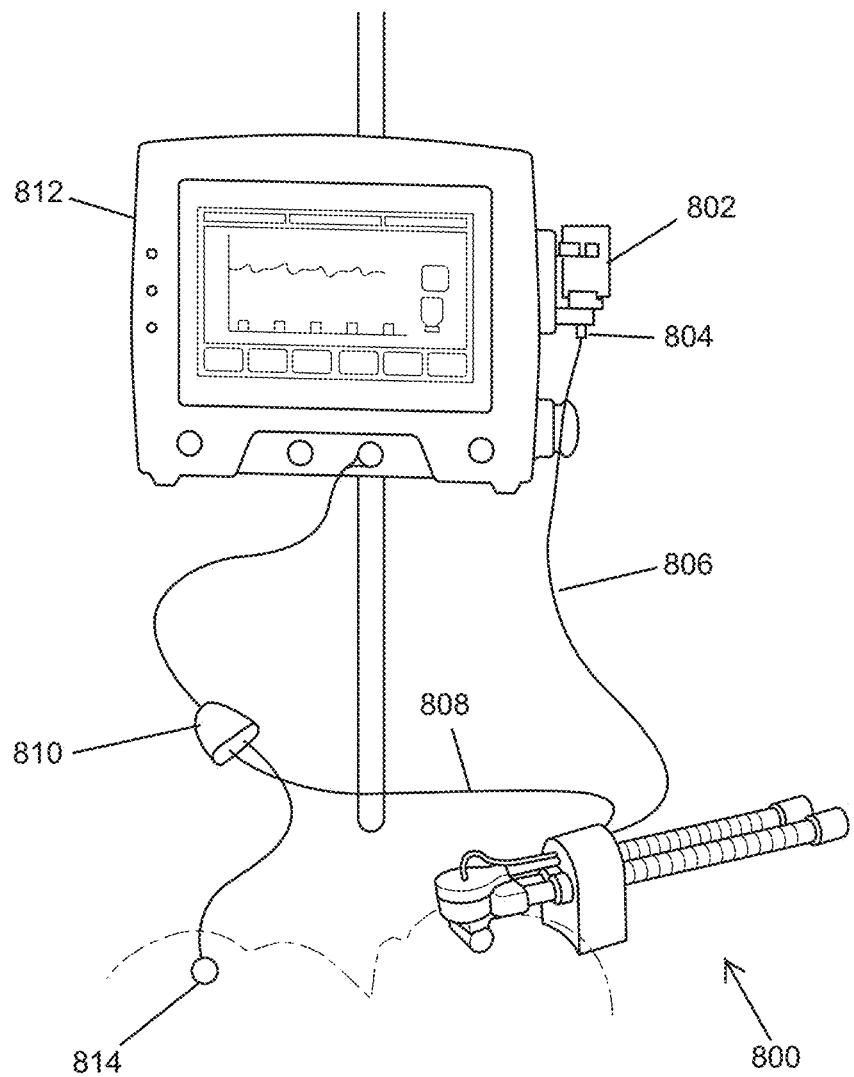
FIG. 9 illustrates the aerosolization device of FIG. 8 connected with the medication source and a controller.
Figure 10:
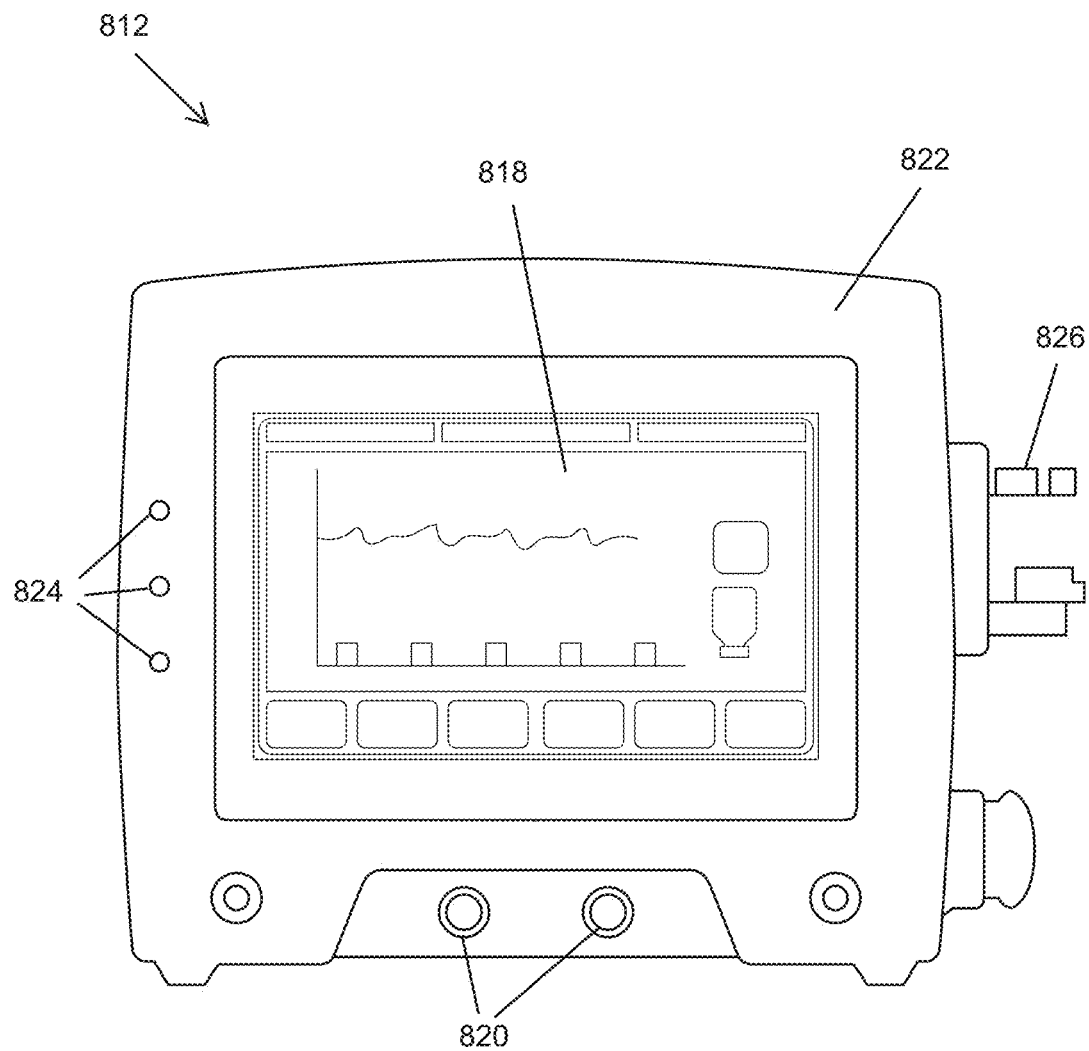
FIG. 10 illustrates the controller of FIG. 9.
Figure 11:
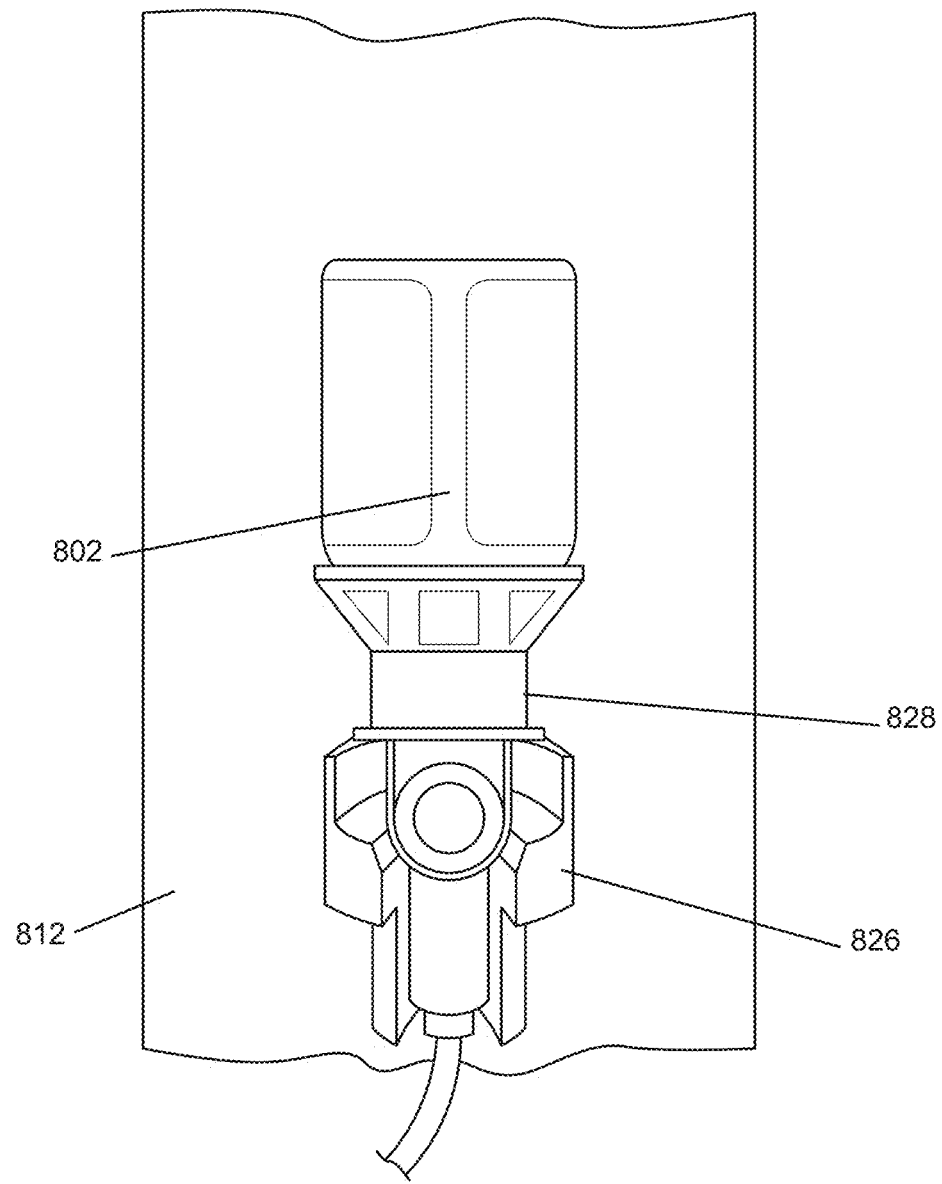
FIG. 11 illustrates a vial holder of the controller of FIG. 9.
Figure 12:
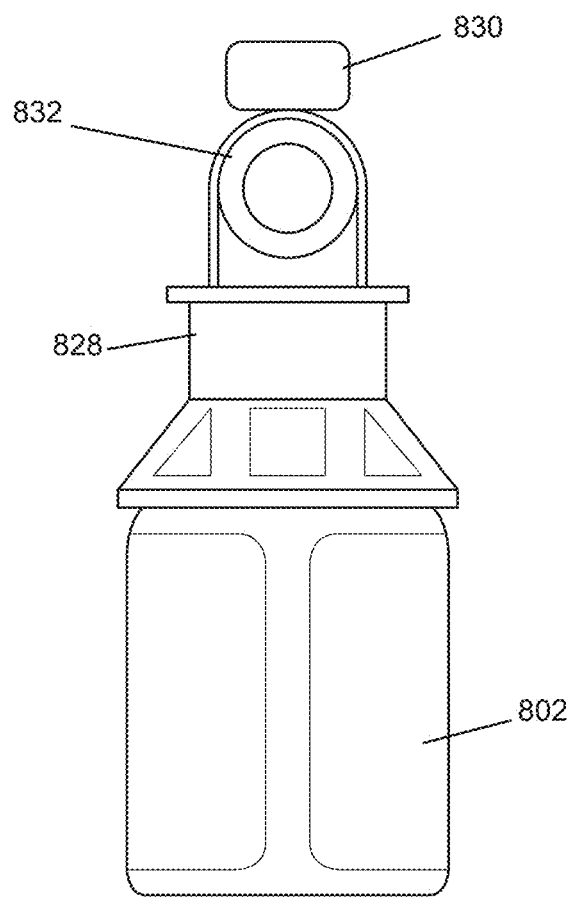
FIG. 12 illustrates the medication source of FIG. 9.

FIG. 7 illustrates the aerosolization device 600 of FIGS. 6-6D in a connected state with both a fluid supply line 700 and a respiration system 702. As illustrated, a first end of the fluid supply line 700 is coupled with the medication supply port 614. For example, in some embodiments, the medication supply port 614 includes a tip that protrudes outward from a body of the aerosolization device 600. An opening of the fluid supply line 700 may be fitted over the tip, thereby allowing fluids from the fluid supply line 700 to pass through the medication supply port 614 and into the reservoir and/or conduit 634 for subsequent delivery to the aerosol generator 602. A second end (not shown) of the fluid supply line 700 may be coupled with a fluid source, such as a vial (or other type of container) of liquid medicament.

The respiratory adaptor 606 may be coupled with the respiration system 702. As illustrated here, the inlet 608 is coupled with an inspiratory limb 650 of the respiration system 702, while the outlet 616 and expiratory limb 652 are obscured. Air and/or other respiratory gases may pass from the inspiratory limb 650 into the respiratory adaptor 606, where one or more diversion mechanisms, such as valves, baffles, and the like, may divert a portion of the airflow into the aerosol chamber 602 via a fluid path, while a remaining larger portion of the airflow of the respiration system 702 is directed through the expiratory limb 652 by the respiratory adaptor 606.

A nebulizer cable 704 is connected with power connection 640. Nebulizer cable 704 is configured to deliver power to the aerosol generator 602, as well as provide operation commands (such as commands that control when and how long the aerosol generator 602 is actuated. For example, a controller (not shown) may be coupled with the aerosolization device 600 via the nebulizer cable. The controller may monitor a respiratory cycle of the patient using one or more breath sensors. Based on this information, the controller may send signals using the nebulizer cable 704 (or other communications link) that activate a pump to deliver liquid to the aerosol generator 612 and that activate the aerosol generator 612 to aerosolize the medicament.

FIG. 8 illustrates another embodiment of an aerosolization device 800. Aerosolization device 800 may be similar to aerosolization device 600 described above. As illustrated, aerosolization device 800 is coupled with a medication source 802. Medication source 802 may be any container that holds a volume of medicament. As illustrated, medication source 802 is a vial that is coupled to a medication port of the aerosolization device via a Luer connection 804 and length of a fluid supply line 806. Also coupled with the aerosolization device 800 is a nebulizer cable 808 that is connectable with a controller (not shown). The nebulizer cable 808 terminates in a pod 810 that is usable to couple the aerosolization device 800 and/or a respiration sensor with the controller.

FIG. 9 illustrates the aerosolization device 800 connected to medication source 802 and a controller 812. The controller may be configured to cause the liquid medicament to be delivered to the aerosolization device 800 via the fluid supply line 806 and to actuate the aerosolization device 800. In some embodiments, the controller 812 may actuate the aerosolization device 800 based on a detected inhalation of a patient. For example, the controller 812 may be coupled with a respiration sensor 814, which may detect the start, duration, and/or end of an inhalation of the patient. In some embodiments, the respiration sensor 814 may be a sensor similar to a Graseby sensor, which may be positioned against a torso (abdomen and/or chest) of the patient to detect a respiratory cycle of the patient. As such one example, the controller 812 may receive a signal from the respiration sensor 814 that indicates that the patient is starting to inhale. The controller 812 may then send commands that cause a volume of liquid medicament to be supplied to the aerosol generator of the aerosolization device 800 and that cause the aerosol generator to activate to aerosolize the liquid medicament during the inhalation.

In some embodiments, the respiration sensor 814 and/or aerosolization device 800 may be coupled directly to the controller 812. In other embodiments, a pod 810 and/or other adaptor may be used to connect the respiration sensor 814 and/or aerosolization device 800 with the controller 812. For example, in some embodiments connecting the respiration sensor to the pod includes inserting a connection, such as a slip Luer, into a port of the pod 810. In the present embodiment, the respiration sensor 814 may be adhered and/or otherwise affixed to the patient's abdomen to begin sensing inspiration cycles FIG. 10 illustrates the controller 812. Controller 812 includes a user interface 818, such as a display screen. In some embodiments, the user interface 818 may be a touchscreen. The controller 812 may include one or more input devices, such as buttons, dials, keypads, touchscreens, and the like that allow a user to interact with the controller 812 to adjust settings, such as dose level, etc. The controller 812 may also include a number of ports 820 that may be used to connect the controller 812 to peripheral units, such as the aerosolization device 800 and/or respiration sensor 814. In some embodiments, the controller 812 may include one or more indicators 824, such as LEDs, that are configured to alert users of the status of various features. For example, the indicators 824 may inform users about whether the aerosolization device 800 and/or respiration sensor 814 are properly connected, whether a power source 832 of the controller 812 is active (i.e. plugged in and/or whether a battery (if present) is charging or charged), whether any faults in the system have been detected, etc. In some embodiments, the indicators 824 may be integrated into the user interface 818. A housing 822 of the controller 812 may include a holder 826 that is configured to securely receive the medication source 802, as best illustrated in FIG. 11. In this embodiment, the medication source 802 is a vial that is secured in an upside down orientation within the holder 826, allowing the entire contents of the medication source 802 to be drained, pumped, and/or otherwise delivered from the medication source 802 to the aerosolization device 802.

FIG. 12 illustrates medication source 802. Here, medication source 802 is in the form of a vial that is affixed with a vented vial access device (VVAD) 828. The VVAD 828 may include a removable cap 830 that seals an opening of the VVAD 828 when affixed to the VVAD 828. The VVAD 828 may also include a filter 832 that helps minimize aerosols within the vial and fluid supply line 806, minimize surface contamination, and neutralize vial pressure. In use, the cap 830 may be removed and a port (not shown) may be affixed to a Luer connector to couple the medication source 802 to the fluid supply line 806.

In some embodiments, the aerosolization devices described herein include an aerosol generator capable of coupling to a variety of artificial respiration systems. The aerosol generator may receive liquid medicament from a fluid source through a fluid delivery conduit. In operation, fluid from the fluid source is pumped with a pump through the fluid delivery conduit to the aerosol generator where the fluid is aerosolized before and/or while the patient inhales. In some embodiments, the fluid delivery conduit may be primed with fluid before treatment to ensure rapid delivery (e.g., preloading fluid in aerosol generator). The pump may controlled with a controller, which times delivery and dosage of the fluid.

The controller includes one or more processors that execute instructions stored on one or more memory to drive operation of the pump and the aerosol generator. For example, the memory may include instructions that indicate the amount of fluid to be pumped to the aerosol generator in each dose for each actuation of the aerosol generator, how much fluid is to be pumped over a specific period of time or times, etc. The stored instructions may be based on a size of the patient, age of the patient, sex of the patient, type of medicament, fluid additives, desired amount of aerosol, etc. The memory also includes instructions for activating the aerosol generator. As illustrated, the controller connects to the aerosol generator with a cable (i.e., electric cable), although in some embodiments the controller may be wirelessly connected to the aerosol generator. The cable carries a signal that activates a piezoelectric (or other) actuator inside the aerosol generator. As the piezoelectric actuator operates, it vibrates a vibratable member that then aerosolizes the fluid for delivery to the patient (i.e., through inhalation). The memory may therefore include instructions for controlling when the piezoelectric actuator starts, stops, vibration frequency or frequencies, etc.

The aerosolization systems described herein may increase treatment effectiveness by timing the creation of the aerosol. For example, the aerosol delivery system may begin aerosolizing the medicament before the patient inhales. In this way, the aerosol delivery system takes advantage of the increased airflow at the start of inhalation. This increases the medicament delivery to the patient as the inhaled air carries the medicament farther into the patient's lungs. The aerosol delivery system may also aerosolize medicament as soon as inhalation is detected (e.g., for spontaneous breathing).

The aerosol delivery system coordinates delivery of the medicament using one or more breath sensors to determine when a patient inhales and for how long. These breath sensors may communicate with the controller through wired connections and/or wireless connections. In some embodiments, the aerosol delivery system may use a combination of breath sensors to provide redundancy and/or more accurate monitoring of the patient's breathing cycle. As just one example, the aerosol delivery system may use a flow sensor in combination with a radar sensor to monitor both airflow and chest movement. As another example, the aerosol delivery system may use a flow sensor, a radar sensor, and plethysmography sensor to monitor the breathing cycle. It will be appreciated that any number and/or any combination of breath sensors may be utilized in a given application to monitor the patient's breathing cycle.

In some embodiments, the flow sensor couples to a gas delivery conduit to sense changes in airflow during inhalation (e.g., mandatory, assisted, or spontaneous breathing). In some embodiments, the flow sensor may also couple to a gas return conduit to detect the start and end of exhalation. And in still other embodiments, the aerosol delivery system may include flow sensors that couple to the gas delivery conduit and the gas return conduit. As the controller receives data from the flow sensor(s), the controller may monitor breathing patterns to predict when the patient is going to breath. The ability to predict when inhalation begins enables the aerosol delivery system to prepare aerosolized medicament for immediate inhalation. More specifically, the aerosol delivery system is able to preload fluid on a vibratable member in the aerosol generator so that the fluid can be aerosolized before inhalation. Because flow detection is not a lagging indicator, the flow sensor can rapidly detect unusual or spontaneous inhalation for aerosol delivery (e.g., less than 10 milliseconds from the start of inhalation).

Predicting the patient's inhalation may begin by using one or more breath and/or flow sensors to tracking the patient's breathing pattern and/or a ventilation cycle (if a patient is mandatorily ventilated). The controller then uses the tracked data to predict when subsequent inhalations will begin. This allows the controller to direct the pump to deliver fluid from the fluid source to the aerosol generator 16 prior to an inhalation. The controller may also signal the aerosol generator to begin aerosolizing the fluid at a proper time, such as within a predetermined time period (e.g., +/−0.5 seconds) before and/or during the predicted inhalation. In this way, aerosol is ready for the patient at the start of inhalation. While the aerosol delivery system is able to predict the breath cycle to produce aerosol for the patient, the aerosol delivery system is also able to recognize spontaneous/irregular breathing not part of the normal pattern using the breath sensors. Once a spontaneous breath is recognized, the aerosol delivery system may immediately pump fluid to the aerosol generator for delivery to the patient.

Figure 13:
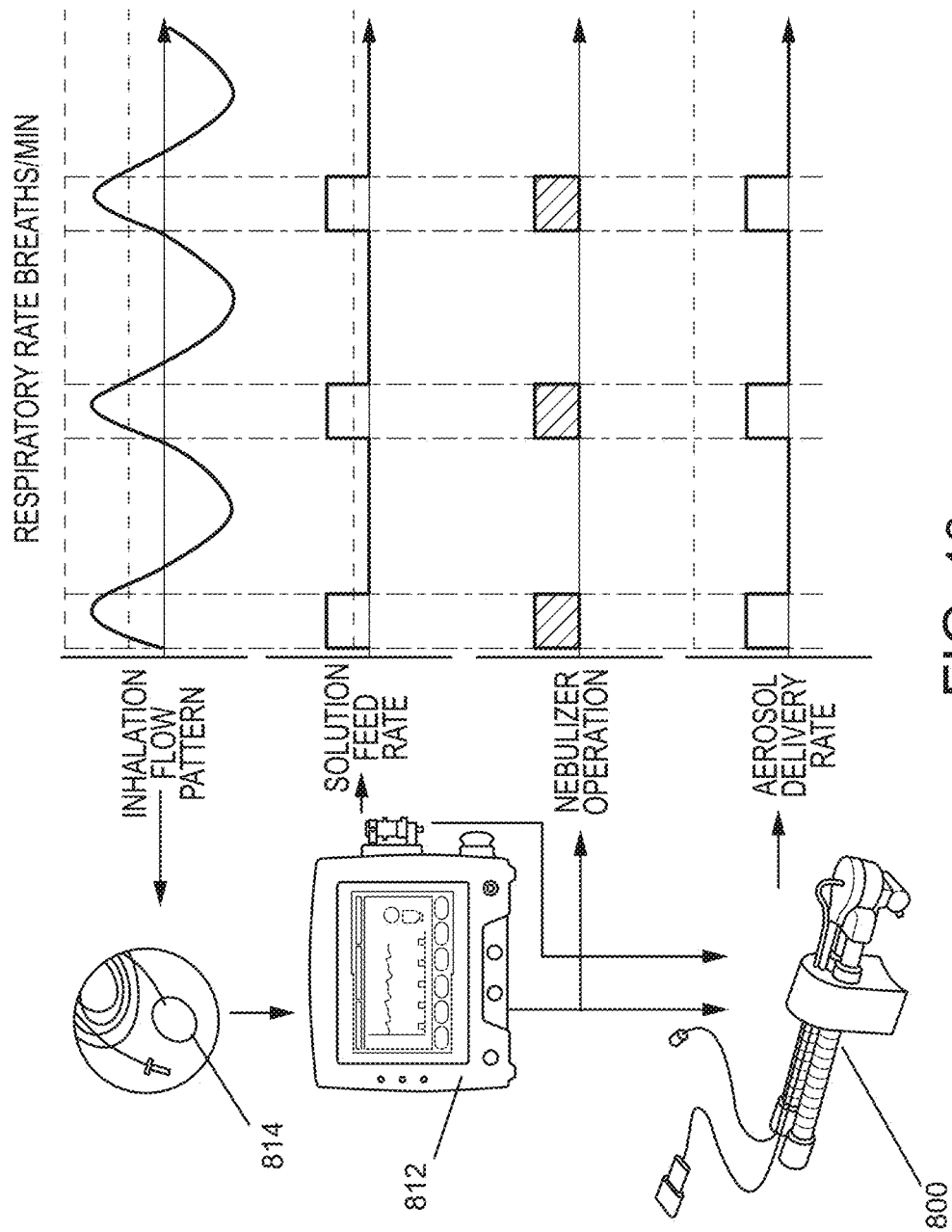
FIG. 13 illustrates functionality of the controller of FIG. 9.

FIG. 13 illustrates one example of the functionality of the controller 812. As shown in plot A, the controller 812 receives a signal from the respiration sensor 814 that indicates that the patient has begun an inhalation. The controller 812 then sends commands that initiate the delivery of a volume of medicament to the aerosol generator, which activates to aerosolize the liquid medicament as illustrated in plots B-D. In some embodiments, the controller 812 may be programmed to cause the aerosolization of medicament only for a first portion of an inhalation, allowing for a final portion of the inhalation to drawn in chase air to help deliver the aerosolized medicament into the deep lungs. For example, as shown in the various plots, the controller 812 causes the aerosolization of medicament only within the first 80% of each inhalation, allowing the final 20% of each inhalation to draw chase air into the patient's airways. It will be appreciated that other aerosolization patterns may be used. For example, the aerosolization of medicament may be done within the first 50%-90% (more commonly between 60%-80% and even more commonly between 70% and 80%) of each inhalation. Times greater than 80% are associated with more aerosol in the upper airway that is exhaled prior to reaching the lower airways. This allows the final 10%-50% (more commonly between about 20%-40% and even more commonly between 20% and 30%) of the inhalation to be used to draw chase air into the patient's airways.

Figure 14:
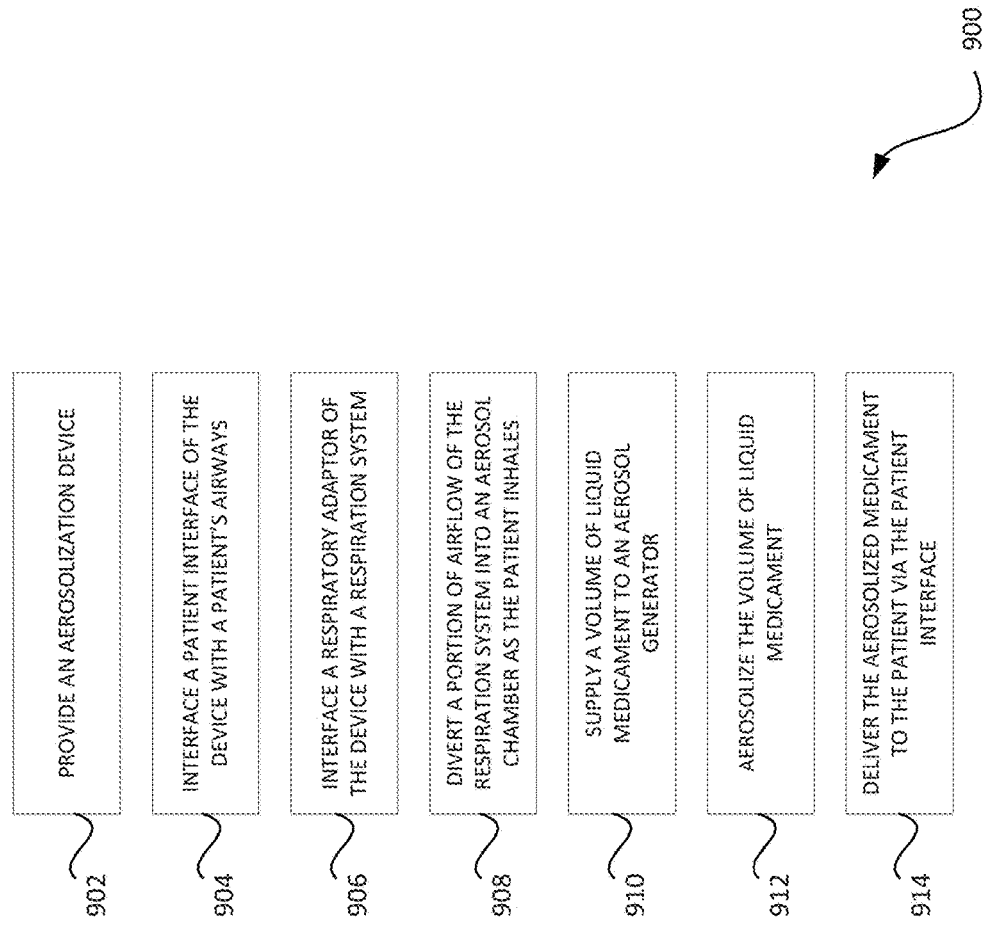
FIG. 14 is a flowchart of a process of delivering aerosolized medicament to a patient.

FIG. 14 is a flowchart of a process 900 for delivering aerosolized medicament to a patient. Process 900 may begin at block 902 by providing an aerosolization device. The aerosolization device may be similar to any of those described herein. For example, the aerosolization device may include an aerosol chamber, a respiratory adaptor, an aerosol generator positioned at a first end of the aerosol chamber opposite the first end and a patient interface positioned at a second end of the aerosol chamber. Process 900 also includes interfacing the patient interface with a patient's airway at block 904. In some embodiments, the patient interface may include nasal prongs that may be inserted into a patient's nares. In some embodiments, the nasal prongs may be removably secured to the aerosolization device such that prongs of different sizes may be affixed to the aerosolization device to accommodate patients of different sizes. At block 906, the respiratory adaptor may be interfaced with a respiration system. For example, the repository adaptor may include an inlet that may be coupled with an inspiratory limb of the respiration system and an outlet that may be coupled with an expiratory limb of the respiration system.

Once the aerosolization device has been interfaced with the patient and the respiration system, block 908 may include diverting a portion of airflow of the respiration system into the aerosol chamber using the respiratory adaptor as the patient inhales. For example, the respiratory adaptor may include one or more baffles that are configured to direct a majority of the airflow through the respiration system to the expiratory limb, while introducing a small amount of the airflow into the aerosol chamber via a fluid channel. At block 910, a volume of liquid medicament may be supplied to the aerosol generator. At block 912, the volume of liquid medicament is aerosolized within the aerosolization chamber using the aerosol generator to generate particles having a mass mean aerodynamic diameter (MMAD) of less than about 3 µm at a rate of at least 0.1 ml/min that mix with the airflow that has been introduced into the chamber. For example, the liquid medicament may be supplied to a mesh, such as a PDAP mesh, which may then be vibrated to aerosolize the liquid medicament. The mixture of aerosolized medicament and the airflow to the patient via the patient interface at block 914.

In some embodiments, the process may include sensing an inhalation of the patient using one or more breath sensors. In such embodiments, the aerosolization of the volume of liquid medicament is triggered based on the sensed inhalation of the patient. For example, the respiration sensor may detect an inhalation. A controller (such as controller 812) may receive an indication of the inhalation and send commands that initiate the delivery of a volume of medicament to the aerosol generator, which activates to aerosolize the liquid medicament. In some embodiments, the controller 812 may be programmed to cause the aerosolization of medicament only for a first portion of an inhalation, allowing for a final portion of the inhalation to drawn in chase air to help deliver the aerosolized medicament into the deep lungs.

EXAMPLES

Figure 15:
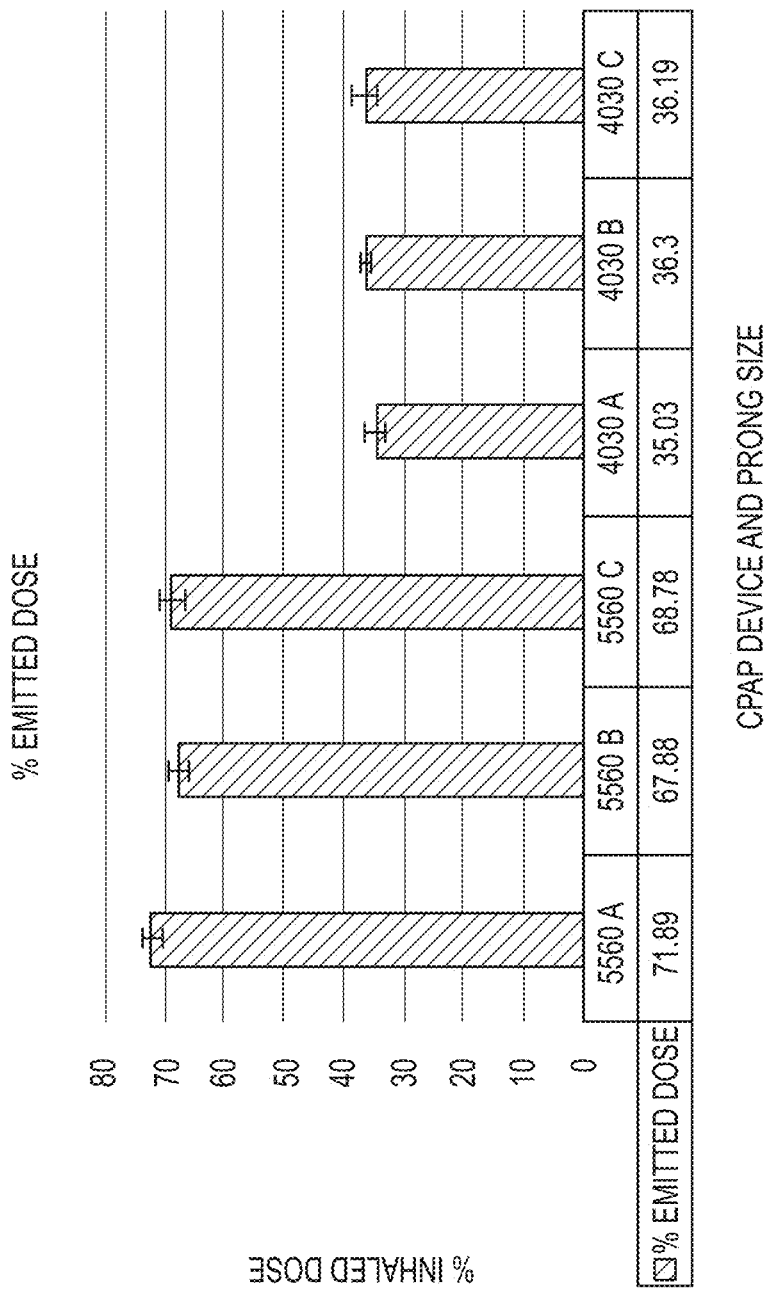
FIG. 15 is a bar graph illustrating emitted dose rates using an aerosolization device according to embodiments.

In vitro experiments were conducted to determine the effective emitted dose of medicament using an aerosolization device in accordance with the present invention. Simulated infant inhalations (volumes, rates and inspiratory: expiratory ratios were performed using a test lung (Ingmar) and/or modified small animal ventilator (Harvard Apparatus) connected distal to a collecting filter that is interfaced with a patient adaptor (here in the form of nasal prongs) of an aerosolization device similar to that described in FIGS. 6-6D. Simulations were performed using two different sizes of nasal prongs, with a larger nasal prong (5560) and a smaller nasal prong (4030). As seen in the bar graph illustrated in FIG. 15, the larger the prong size, the higher the emitted dose. Notably, the larger nasal prong (5560) resulted in emitted doses of between 68% and 72% emitted dose while the smaller nasal prong (4030) resulted in emitted doses of between about 35% and 37%.

Figure 16:
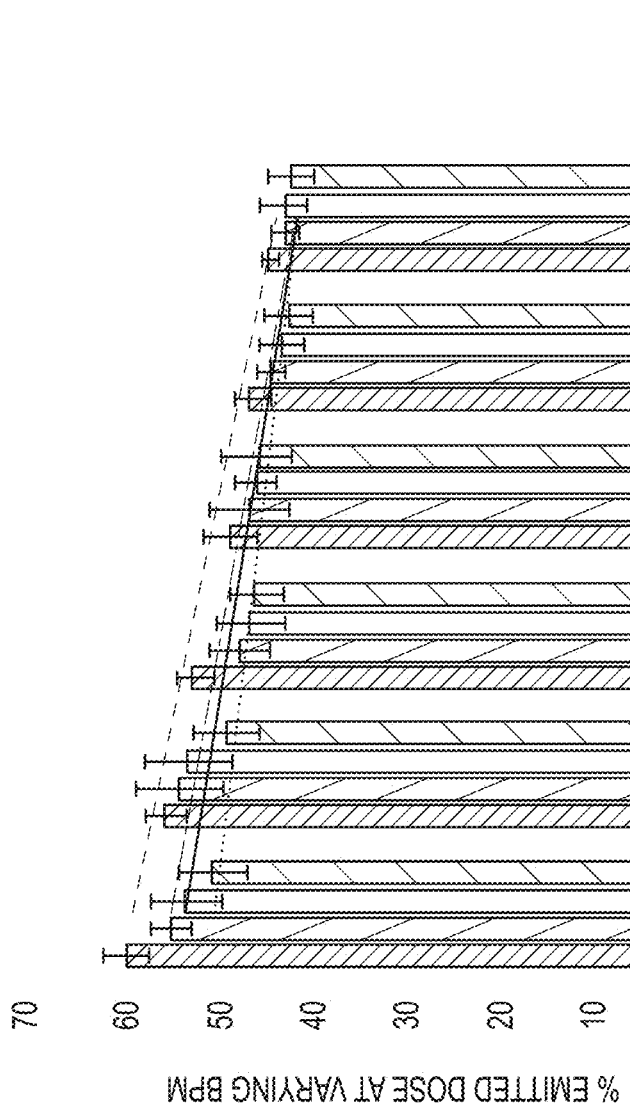
FIG. 16 is a bar graph illustrating emitted dose rates as a function of breathing rate and flow rate using an aerosolization device according to embodiments.

The air flow was then set to 6 liters per minute (LPM), 8 LPM, and 10 LPM and with breathing rates of 60 breaths per minute (BPM), 80 BPM, 100 BPM, and 120 BPM. Emitted dose rates were then measured at each combination of air flow rate and breathing rate. As illustrated in FIG. 16, gas flow has an effect on delivery efficiency, with greater flow rates leading to slightly lower delivery efficiencies. For example, at lower flow rates (6 LPM), the larger nasal prongs (5560) resulted in approximately 50% to about 60% emitted dose at the extreme ends of the tested breathing rates, while at higher flow rates (10 LPM) the emitted dose ranged from about 42% to about 47%. It is noted that as the breathing rates increased, the difference in efficiency associated with greater flow rates becomes less pronounced. For example, the range of emitted dose rates at 60 BPM was about 44% to about 60%, while at 120 BPM the emitted dose rates ranged from about 42% to about 51%. Based on these results, it was determined that the aerosol generators described herein enables consistent inhaled dose of medicament across a clinically relevant range of respiratory rates (60-120 BPM) and CPAP flows (6-10 LPM) commonly used with bubble and vent CPAP systems.

The methods, systems, and devices discussed above are examples. Some embodiments were described as processes depicted as flow diagrams or block diagrams. Although each may describe the operations as a sequential process, many of the operations can be performed in parallel or concurrently. In addition, the order of the operations may be rearranged. A process may have additional steps not included in the figure. Furthermore, embodiments of the methods may be implemented by hardware, software, firmware, middleware, microcode, hardware description languages, or any combination thereof. When implemented in software, firmware, middleware, or microcode, the program code or code segments to perform the associated tasks may be stored in a computer-readable medium such as a storage medium. Processors may perform the associated tasks.

It should be noted that the systems and devices discussed above are intended merely to be examples. It must be stressed that various embodiments may omit, substitute, or add various procedures or components as appropriate. Also, features described with respect to certain embodiments may be combined in various other embodiments. Different aspects and elements of the embodiments may be combined in a similar manner. Also, it should be emphasized that technology evolves and, thus, many of the elements are examples and should not be interpreted to limit the scope of the invention.

Specific details are given in the description to provide a thorough understanding of the embodiments. However, it will be understood by one of ordinary skill in the art that the embodiments may be practiced without these specific details. For example, well-known structures and techniques have been shown without unnecessary detail in order to avoid obscuring the embodiments. This description provides example embodiments only, and is not intended to limit the scope, applicability, or configuration of the invention. Rather, the preceding description of the embodiments will provide those skilled in the art with an enabling description for implementing embodiments of the invention. Various changes may be made in the function and arrangement of elements without departing from the spirit and scope of the invention.

The methods, systems, devices, graphs, and tables discussed above are examples. Various configurations may omit, substitute, or add various procedures or components as appropriate. For instance, in alternative configurations, the methods may be performed in an order different from that described, and/or various stages may be added, omitted, and/or combined. Also, features described with respect to certain configurations may be combined in various other configurations. Different aspects and elements of the configurations may be combined in a similar manner. Also, technology evolves and, thus, many of the elements are examples and do not limit the scope of the disclosure or claims. Additionally, the techniques discussed herein may provide differing results with different types of context awareness classifiers.

While illustrative and presently preferred embodiments of the disclosed systems, methods, and machine-readable media have been described in detail herein, it is to be understood that the inventive concepts may be otherwise variously embodied and employed, and that the appended claims are intended to be construed to include such variations, except as limited by the prior art.

Unless defined otherwise, all technical and scientific terms used herein have the same meaning as commonly or conventionally understood. As used herein, the articles "a" and "an" refer to one or to more than one (i.e., to at least one) of the grammatical object of the article. By way of example, "an element" means one element or more than one element. "About" and/or "approximately" as used herein when referring to a measurable value such as an amount, a temporal duration, and the like, encompasses variations of ±20% or ±10%, ±5%, or +0.1% from the specified value, as such variations are appropriate to in the context of the systems, devices, circuits, methods, and other implementations described herein. "Substantially" as used herein when referring to a measurable value such as an amount, a temporal duration, a physical attribute (such as frequency), and the like, also encompasses variations of ±20% or ±10%, ±5%, or +0.1% from the specified value, as such variations are appropriate to in the context of the systems, devices, circuits, methods, and other implementations described herein. As used herein, including in the claims, "and" as used in a list of items prefaced by "at least one of" or "one or more of" indicates that any combination of the listed items may be used. For example, a list of "at least one of A, B, and C" includes any of the combinations A or B or C or AB or AC or BC and/or ABC (i.e., A and B and C). Furthermore, to the extent more than one occurrence or use of the items A, B, or C is possible, multiple uses of A, B, and/or C may form part of the contemplated combinations. For example, a list of "at least one of A, B, and C" may also include AA, AAB, AAA, BB, etc.

Having described several embodiments, it will be recognized by those of skill in the art that various modifications, alternative constructions, and equivalents may be used without departing from the spirit of the invention. For example, the above elements may merely be a component of a larger system, wherein other rules may take precedence over or otherwise modify the application of the invention. Also, a number of steps may be undertaken before, during, or after the above elements are considered. Accordingly, the above description should not be taken as limiting the scope of the invention.

Also, the words "comprise", "comprising", "contains", "containing", "include", "including", and "includes", when used in this specification and in the following claims, are intended to specify the presence of stated features, integers, components, or steps, but they do not preclude the presence or addition of one or more other features, integers, components, steps, acts, or groups.

What is claimed:

1. An aerosolization device, comprising:
an aerosol chamber having a first end and a second end;
an aerosol generator positioned at the first end of the aerosol chamber, wherein the aerosol generator comprises a vibratable mesh that is configured to aerosolize a volume of medicament into particles having a mass mean aerodynamic diameter (MMAD) of between 2 μm and 3 μm at a rate of at least 0.1 ml/min;
a patient interface that is positioned proximate the second end of the aerosol chamber; and
a respiratory adaptor that is configured to couple the aerosolization device with a respiration system and to divert a portion of airflow of the respiration system to the aerosol chamber via a fluid channel, wherein:
the respiratory adaptor comprises a first baffle that defines a first airway and a second baffle that defines a second airway, the first baffle and the second baffle being configured to divert the portion of airflow from the respiration system into the aerosol chamber via the fluid channel and to divert an additional portion of airflow from an inspiratory limb to an expiratory limb; and
the aerosol chamber is configured to mix the portion of the airflow with the aerosolized medicament from the aerosol generator for subsequent delivery to a patient via the patient interface.

2. The aerosolization device of claim 1, wherein:
the aerosol generator comprises a reservoir that is configured to receive the volume of the medicament for aerosolization by the aerosol generator.

3. The aerosolization device of claim 1, wherein:
the portion of airflow is respiratory flow and is less than an amount of air that continues to the expiratory limb of the respiration system.

4. The aerosolization system of claim 1, wherein:
the first airway is provided at a lateral end of the first baffle;
the second airway is provided beyond a distal edge of the second baffle; and
the lateral end and the distal edge extend in different directions such that the respiratory flow moves in multiple directions to pass the first baffle and the second baffle.

5. The aerosolization device of claim 1, further comprising:
a conduit that is configured to deliver the volume of medicament to the aerosol generator, wherein:
a distalmost tip of the conduit has a diameter; and
the distalmost tip of the conduit is positioned at a distance from the mesh that is less than or equal to the diameter.

6. The aerosolization device of claim 1, wherein:
the aerosol chamber is generally funnel-shaped such that the first end comprises a wide portion of the aerosol chamber and the second end comprises a narrow portion of the aerosol chamber.

7. The aerosolization device of claim 1, wherein:
the patient interface comprises nasal prongs.

8. The aerosolization device of claim 1, wherein:
a fluid path defined by the fluid channel forms an angle of no greater than 90 degrees with an upstream side of a flow path through the respiration system.

9. The aerosolization device of claim 1, wherein:
the respiratory adaptor comprises:
an inlet that is configured to interface with the inspiratory limb of the respiration system; and
an outlet that is configured to interface with the expiratory limb of the respiration system.

10. The aerosolization device of claim 9, wherein:
the fluid channel is positioned such that a respiratory flow does not enter the aerosol chamber between breaths of the patient.

11. The aerosolization device of claim 1, further comprising:
a fluid supply line coupled with aerosolization device; and
a pump configured to deliver the volume of medicament to a reservoir of the aerosolization device via the fluid supply line.

12. The aerosolization device of claim 1, wherein:
the medicament comprises a surfactant.

13. An aerosolization device, comprising:
an aerosol chamber;
an aerosolization generator positioned at a first end of the aerosol chamber, wherein the aerosolization generator comprises a vibratable mesh that is configured to aerosolize a volume of medicament into particles having a mass mean aerodynamic diameter (MMAD) of between 2 µm and 3 µm at a rate of at least 0.1 ml/min;
a patient interface positioned at a second end of the aerosol chamber that is opposite the first end;
an inlet that is configured to couple with an inspiratory limb of a respiration system;
an outlet that is configured to couple with an expiratory limb of the respiration system;
a fluid channel coupling the aerosol chamber with at least one of the inlet and the outlet;
a first baffle that defines a first airway; and
a second baffle that defines a second airway, the first baffle and the second baffle being configured to divert a portion of airflow from the respiration system into the aerosol chamber via the fluid channel and to divert an additional portion of airflow from the inspiratory limb to the expiratory limb, wherein:
the fluid channel is disposed such that the aerosol chamber is isolated from continuous flow passing from the inlet to the outlet; and
the aerosol chamber is configured to mix respiratory flow received from the respiration system via the fluid channel with the aerosolized medicament from the aerosolization device.

14. The aerosolization device of claim 13, wherein:
the aerosol chamber is generally funnel-shaped such that the first end comprises a wide portion of the aerosol chamber and the second end comprises a narrow portion of the aerosol chamber.

15. The aerosolization device of claim 13, wherein:
the patient interface comprises nasal prongs or a nasal mask.

16. The aerosolization device of claim 13, wherein:
a fluid path defined by the fluid channel forms an acute angle with an upstream side of the at least one of one of the inlet and the outlet with which the fluid channel is coupled.

17. The aerosolization device of claim 13, wherein:
the inlet and the outlet are configured to direct a flow of gas from the inspiratory limb to the expiratory limb such that the respiratory flow does not enter the aerosol chamber between breaths of the patient.

18. The aerosolization device of claim 13, further comprising:
a fluid supply line coupled with aerosolization device; and
a pump configured to deliver a volume of medicament to a conduit of the aerosolization device via the fluid supply line.

19. The aerosolization device of claim 13, wherein:
the inlet and the outlet are integrally formed.

20. A method of delivering aerosolized medicament to a patient, comprising:
providing an aerosolization device comprising:
an aerosol chamber;
a respiratory adaptor;
an aerosol generator positioned at a first end of the aerosol chamber opposite a second end, the aerosol generator comprising a vibratable mesh; and
a patient interface positioned at the second end of the aerosol chamber;
interfacing the patient interface with a patient's airway;
interfacing the respiratory adaptor with a respiration system, wherein:
the respiratory adaptor comprises a first baffle that defines a first airway and a second baffle that defines a second airway, the first baffle and the second baffle being configured to divert a portion of airflow from the respiration system into the aerosol chamber via a fluid channel and to divert an additional portion of airflow from an inspiratory limb to an expiratory limb;
diverting a portion of airflow of the respiration system into the aerosol chamber using the respiratory adaptor as the patient inhales;
supplying a volume of liquid medicament to the vibratable mesh of the aerosol generator;
aerosolizing, using the vibratable mesh, the volume of liquid medicament within the aerosolization chamber using the aerosol generator to generate particles having a mass mean aerodynamic diameter (MMAD) of between 2 µm and 3 µm at a rate of at least 0.1 ml/min that mix with the airflow that has been introduced into the chamber; and
delivering the mixture of the aerosolized medicament and the airflow to the patient via the patient interface.

21. The method of delivering aerosolized medicament to a patient of claim 20, further comprising:
sensing an inhalation of the patient using one or more breath sensors.

22. The method of delivering aerosolized medicament to a patient of claim 21, wherein:
the aerosolization of the volume of liquid medicament is triggered based on the sensed inhalation of the patient.

23. The method of delivering aerosolized medicament to a patient of claim 20, wherein:
the aerosol chamber is generally funnel-shaped such that the first end comprises a wide portion of the aerosol chamber and the second end comprises a narrow portion of the aerosol chamber.

24. The method of delivering aerosolized medicament to a patient of claim 20, wherein:
the airflow is drawn into the aerosol chamber by a vacuum created by an inhalation of the patient at the patient interface.

25. The method of delivering aerosolized medicament to a patient of claim 20, wherein:
the respiratory adaptor comprises an inlet and an outlet; and
the aerosol chamber is coupled with at least one of the inlet or the outlet via a fluid channel, wherein the fluid channel is disposed such that the aerosol chamber is isolated from continuous flow passing from the inlet to the outlet.

* * * * *